United States Patent
Blain

(10) Patent No.: US 7,998,172 B2
(45) Date of Patent: Aug. 16, 2011

(54) VERTEBRAL FACET JOINT PROSTHESIS AND METHOD OF FIXATION

(75) Inventor: Jason Blain, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 12/425,298

(22) Filed: Apr. 16, 2009

(65) Prior Publication Data

US 2009/0204152 A1   Aug. 13, 2009

Related U.S. Application Data

(62) Division of application No. 10/865,073, filed on Jun. 10, 2004, now Pat. No. 7,846,183.

(60) Provisional application No. 60/542,351, filed on Feb. 6, 2004, provisional application No. 60/542,769, filed on Feb. 6, 2004, provisional application No. 60/542,350, filed on Feb. 6, 2004.

(51) Int. Cl.
*A61B 17/70* (2006.01)

(52) U.S. Cl. ...................................... 606/247

(58) Field of Classification Search .......... 606/246–247, 606/232–233; 623/13.14, 16.11, 17.11
See application file for complete search history.

(56) References Cited

U.S. PATENT DOCUMENTS

| 3,867,728 A | 2/1975 | Stubstad et al. |
| 3,875,595 A | 4/1975 | Froning |
| 3,879,767 A | 4/1975 | Stubstad |
| 4,001,896 A | 1/1977 | Arkangel |
| 4,085,466 A | 4/1978 | Goodfellow et al. |
| 4,156,296 A | 5/1979 | Johnson et al. |
| 4,231,121 A | 11/1980 | Lewis |
| 4,349,921 A | 9/1982 | Kuntz |
| 4,502,161 A | 3/1985 | Wall |
| 4,634,445 A | 1/1987 | Helal |
| 4,714,469 A | 12/1987 | Kenna |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,863,477 A | 9/1989 | Monson |

(Continued)

FOREIGN PATENT DOCUMENTS

CA    2437575    4/2009

(Continued)

OTHER PUBLICATIONS

3$^{rd}$ Party lab notebook, 2 pages, dated May 20, 2003.

(Continued)

*Primary Examiner* — Eduardo C Robert
*Assistant Examiner* — Elana Fisher
(74) *Attorney, Agent, or Firm* — Knobbe, Martens, Olson & Bear, LLP.

(57) ABSTRACT

Devices and methods for altering the spacing and motion at the facet joints of the vertebral column are provided. One embodiment of the invention comprises a prosthesis with surfaces configured to articulate with the facets of the facet joint. A retaining member for anchoring the prosthesis within the facet joint is optionally included. Methods for surgically and less invasively implanting the prosthesis and securing the prosthesis to the articular processes or surrounding soft tissue are also provided.

12 Claims, 29 Drawing Sheets

U.S. PATENT DOCUMENTS

| | | | |
|---|---|---|---|
| 4,904,260 A | 2/1990 | Ray et al. | |
| 4,911,718 A | 3/1990 | Lee et al. | |
| 4,919,667 A | 4/1990 | Richmond | |
| 4,936,848 A | 6/1990 | Bagby | |
| 4,969,909 A | 11/1990 | Barouk | |
| 5,000,165 A | 3/1991 | Watanabe | |
| 5,015,255 A | 5/1991 | Kuslich | |
| 5,047,055 A | 9/1991 | Bao et al. | |
| 5,062,845 A | 11/1991 | Kuslich et al. | |
| 5,071,437 A | 12/1991 | Steffee | |
| 5,092,866 A | 3/1992 | Breard et al. | |
| 5,127,912 A | 7/1992 | Ray et al. | |
| 5,147,404 A | 9/1992 | Downey | |
| 5,171,280 A | 12/1992 | Baumgartner | |
| 5,192,326 A | 3/1993 | Bao et al. | |
| 5,258,031 A | 11/1993 | Salib et al. | |
| 5,300,073 A | 4/1994 | Ray et al. | |
| 5,306,275 A | 4/1994 | Bryan | |
| 5,306,308 A | 4/1994 | Gross et al. | |
| 5,306,309 A | 4/1994 | Wagner et al. | |
| 5,360,431 A | 11/1994 | Puno et al. | |
| 5,370,697 A | 12/1994 | Baumgartner | |
| 5,401,269 A | 3/1995 | Buttner-Janz et al. | |
| 5,415,661 A | 5/1995 | Holmes | |
| 5,425,773 A | 6/1995 | Boyd et al. | |
| 5,437,672 A | 8/1995 | Alleyne | |
| 5,445,639 A | 8/1995 | Kuslich et al. | |
| 5,458,642 A | 10/1995 | Beer et al. | |
| 5,458,643 A | 10/1995 | Oka et al. | |
| 5,491,882 A | 2/1996 | Walston et al. | |
| 5,496,318 A | 3/1996 | Howland et al. | |
| 5,507,823 A | 4/1996 | Walston et al. | |
| 5,514,180 A | 5/1996 | Heggeness et al. | |
| 5,527,312 A | 6/1996 | Ray | |
| 5,527,314 A | 6/1996 | Brumfield et al. | |
| 5,534,028 A | 7/1996 | Bao et al. | |
| 5,534,030 A | 7/1996 | Navarro et al. | |
| 5,545,229 A | 8/1996 | Parsons et al. | |
| 5,556,431 A | 9/1996 | Buttner-Janz | |
| 5,562,738 A | 10/1996 | Boyd et al. | |
| 5,571,189 A | 11/1996 | Kuslich | |
| 5,571,191 A | 11/1996 | Fitz | |
| 5,577,995 A | 11/1996 | Walker et al. | |
| 5,586,989 A | 12/1996 | Bray, Jr. | |
| 5,591,165 A | 1/1997 | Jackson | |
| 5,603,713 A | 2/1997 | Aust et al. | |
| 5,638,700 A | 6/1997 | Shechter | |
| 5,645,597 A | 7/1997 | Krapiva | |
| 5,645,599 A | 7/1997 | Samani | |
| 5,653,762 A | 8/1997 | Pisharodi | |
| 5,674,295 A | 10/1997 | Ray et al. | |
| 5,674,296 A | 10/1997 | Bryan et al. | |
| 5,676,701 A | 10/1997 | Yuan et al. | |
| 5,683,464 A | 11/1997 | Wagner et al. | |
| 5,683,466 A | 11/1997 | Vitale | |
| 5,702,450 A | 12/1997 | Bisserie | |
| 5,707,373 A | 1/1998 | Sevrain et al. | |
| 5,716,415 A | 2/1998 | Steffee | |
| 5,741,261 A | 4/1998 | Moskovitz et al. | |
| 5,766,251 A | 6/1998 | Koshino | |
| 5,766,253 A | 6/1998 | Brosnahan, III | |
| 5,772,663 A | 6/1998 | Whiteside et al. | |
| 5,824,093 A | 10/1998 | Ray et al. | |
| 5,824,094 A | 10/1998 | Serhan et al. | |
| 5,836,948 A | 11/1998 | Zucherman et al. | |
| 5,860,977 A | 1/1999 | Zucherman et al. | |
| 5,865,846 A | 2/1999 | Bryan et al. | |
| 5,868,745 A | 2/1999 | Alleyne | |
| 5,876,404 A | 3/1999 | Zucherman et al. | |
| 5,879,396 A | 3/1999 | Walston et al. | |
| 5,888,203 A | 3/1999 | Goldberg | |
| 5,893,889 A | 4/1999 | Harrington | |
| 5,895,428 A | 4/1999 | Berry | |
| RE36,221 E | 6/1999 | Breard et al. | |
| 5,951,555 A | 9/1999 | Rehak et al. | |
| 5,997,542 A | 12/1999 | Burke | |
| 6,001,130 A | 12/1999 | Bryan et al. | |
| 6,014,588 A | 1/2000 | Fitz | |
| 6,019,792 A | 2/2000 | Cauthen | |
| 6,039,763 A | 3/2000 | Shelokov | |
| 6,048,342 A | 4/2000 | Zucherman et al. | |
| 6,063,121 A | 5/2000 | Xavier et al. | |
| 6,066,325 A | 5/2000 | Wallace et al. | |
| 6,068,630 A | 5/2000 | Zucherman et al. | |
| RE36,758 E | 6/2000 | Fitz | |
| 6,080,157 A | 6/2000 | Cathro et al. | |
| 6,099,531 A | 8/2000 | Bonutti | |
| 6,113,637 A | 9/2000 | Gill et al. | |
| 6,132,464 A | 10/2000 | Martin | |
| 6,132,465 A | 10/2000 | Ray et al. | |
| 6,146,422 A | 11/2000 | Lawson | |
| 6,156,067 A | 12/2000 | Bryan et al. | |
| 6,200,322 B1 | 3/2001 | Branch et al. | |
| 6,293,949 B1 | 9/2001 | Justis et al. | |
| 6,368,350 B1 | 4/2002 | Erickson et al. | |
| 6,379,386 B1 | 4/2002 | Resch et al. | |
| 6,419,703 B1 | 7/2002 | Fallin et al. | |
| 6,436,101 B1 | 8/2002 | Hamada et al. | |
| 6,470,207 B1 | 10/2002 | Simon et al. | |
| 6,565,605 B2 | 5/2003 | Goble et al. | |
| 6,579,318 B2 | 6/2003 | Varga et al. | |
| 6,579,319 B2 | 6/2003 | Goble et al. | |
| 6,589,244 B1 | 7/2003 | Sevrain et al. | |
| 6,610,091 B1 | 8/2003 | Reiley | |
| 6,626,944 B1 | 9/2003 | Taylor | |
| 6,669,729 B2 | 12/2003 | Chin | |
| 6,706,068 B2 | 3/2004 | Ferree | |
| 6,761,720 B1 | 7/2004 | Senegas | |
| 6,764,491 B2 | 7/2004 | Frey et al. | |
| 6,783,527 B2 | 8/2004 | Drewry et al. | |
| 6,811,567 B2 | 11/2004 | Reiley | |
| 6,902,566 B2 | 6/2005 | Zucherman et al. | |
| 6,908,484 B2 | 6/2005 | Zubok et al. | |
| 6,966,930 B2 * | 11/2005 | Arnin et al. | 623/17.11 |
| 6,974,478 B2 | 12/2005 | Reiley et al. | |
| 7,013,675 B2 | 3/2006 | Marquez-Pickering | |
| 7,051,451 B2 | 5/2006 | Augostino et al. | |
| 7,074,238 B2 | 7/2006 | Stinson et al. | |
| 7,101,375 B2 | 9/2006 | Zucherman et al. | |
| 7,223,269 B2 | 5/2007 | Chappuis | |
| 7,371,238 B2 | 5/2008 | Sololeski et al. | |
| 7,517,358 B2 | 4/2009 | Petersen | |
| 2001/0018614 A1 | 8/2001 | Bianchi | |
| 2002/0019637 A1 | 2/2002 | Frey et al. | |
| 2002/0029039 A1 | 3/2002 | Zucherman et al. | |
| 2002/0065557 A1 | 5/2002 | Goble et al. | |
| 2002/0072800 A1 | 6/2002 | Goble et al. | |
| 2002/0077700 A1 | 6/2002 | Varga et al. | |
| 2002/0123806 A1 | 9/2002 | Reiley | |
| 2002/0151895 A1 | 10/2002 | Soboleski et al. | |
| 2002/0198527 A1 | 12/2002 | Muckter | |
| 2003/0004572 A1 | 1/2003 | Goble et al. | |
| 2003/0028250 A1 | 2/2003 | Reiley et al. | |
| 2003/0040797 A1 | 2/2003 | Fallin et al. | |
| 2003/0187454 A1 | 10/2003 | Gill et al. | |
| 2003/0191532 A1 | 10/2003 | Goble et al. | |
| 2003/0204259 A1 | 10/2003 | Goble et al. | |
| 2003/0216669 A1 | 11/2003 | Lang et al. | |
| 2003/0233146 A1 | 12/2003 | Grinberg et al. | |
| 2004/0006391 A1 | 1/2004 | Reiley | |
| 2004/0010318 A1 | 1/2004 | Ferree | |
| 2004/0024462 A1 | 2/2004 | Ferree et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0059429 A1 | 3/2004 | Amin et al. | |
| 2004/0087954 A1 | 5/2004 | Allen et al. | |
| 2004/0116927 A1 | 6/2004 | Graf | |
| 2004/0127989 A1 | 7/2004 | Dooris et al. | |
| 2004/0143264 A1 | 7/2004 | McAfee | |
| 2004/0176844 A1 | 9/2004 | Zubok et al. | |
| 2004/0230201 A1 | 11/2004 | Yuan et al. | |

| | | | |
|---|---|---|---|
| 2004/0230304 | A1 | 11/2004 | Yuan et al. |
| 2005/0010291 | A1 | 1/2005 | Stinson et al. |
| 2005/0015146 | A1 | 1/2005 | Louis et al. |
| 2005/0043797 | A1 | 2/2005 | Lee |
| 2005/0043799 | A1 | 2/2005 | Reiley |
| 2005/0049705 | A1 | 3/2005 | Hale et al. |
| 2005/0055096 | A1 | 3/2005 | Serhan et al. |
| 2005/0131538 | A1 | 6/2005 | Chervitz et al. |
| 2005/0143818 | A1 | 6/2005 | Yuan et al. |
| 2005/0159746 | A1 | 7/2005 | Grob et al. |
| 2005/0197700 | A1 | 9/2005 | Boehm et al. |
| 2006/0004367 | A1 | 1/2006 | Alamin et al. |
| 2006/0036323 | A1 | 2/2006 | Carl et al. |
| 2006/0111782 | A1 | 5/2006 | Petersen |
| 2006/0149375 | A1 | 7/2006 | Yuan et al. |
| 2006/0200137 | A1 | 9/2006 | Soboleski et al. |
| 2007/0149976 | A1 | 6/2007 | Hale et al. |
| 2007/0179619 | A1 | 8/2007 | Grob |
| 2008/0287996 | A1 | 11/2008 | Soboleski et al. |
| 2009/0024166 | A1 | 1/2009 | Carl et al. |
| 2009/0125066 | A1 | 5/2009 | Kraus et al. |

FOREIGN PATENT DOCUMENTS

| | | |
|---|---|---|
| DE | 9304368 | 5/1993 |
| DE | 20112123 | 10/2001 |
| DE | 10135771 | 2/2003 |
| EP | 0322334 | 6/1989 |
| EP | 0392124 | 10/1990 |
| EP | 0610837 | 8/1994 |
| FR | 2722980 | 2/1996 |
| JP | 10179622 A2 | 7/1998 |
| JP | 2007503884 | 3/2007 |
| JP | 2007518524 | 7/2007 |
| MX | 6012309 | 1/2007 |
| WO | WO 93/14721 | 8/1993 |
| WO | WO 98/48717 | 11/1998 |
| WO | WO 99/23963 A1 | 5/1999 |
| WO | WO 00/38582 A1 | 7/2000 |
| WO | WO 00/53126 | 9/2000 |
| WO | WO 01/30248 A1 | 5/2001 |
| WO | 02065954 | 8/2002 |
| WO | WO 03/101350 | 12/2003 |
| WO | WO 2004/071358 A1 | 8/2004 |
| WO | WO 2005/020850 | 3/2005 |
| WO | WO 2005/072661 | 8/2005 |

OTHER PUBLICATIONS

E-mail from 3$^{rd}$ party citing U.S. Appl. No. 60/721,909; U.S. Appl. No. 60/750,005 and U.S. Appl. No. 60/749,000.
International Preliminary Report on Patentability for Application No. PCT/US2005/003753 filed Feb. 4, 2005.
European Examination Report dated Mar. 10, 2008 for Application No. EP05712981 filed Feb. 4, 2005.
European Examination Report dated Apr. 6, 2009 for Application No. EP05712981 filed Feb. 4, 2005.
International Search Report for PCT Application No. PCT/CA2002/00193 (WO 02/065954) filed Feb. 15, 2002.
International Search Report for PCT Application No. PCT/US2004/028094 (WO 05/020850) filed Aug. 27, 2004.
International Preliminary Report on Patentability for PCT Application No. PCT/US2004/028094 (WO 05/020850) filed Aug. 27, 2004.
International Search Report for PCT Application No. PCT/US2005/000987 (WO 05/072661) filed Jan. 13, 2005.
International Preliminary Report on Patentability for PCT Application No. PCT/US2005/000987 (WO 05/072661) filed Jan. 13, 2005.
PARTEQ Innovations, "Facet Joint Implants & Resurfacing Devices," Technology Opportunity Bulletin, Tech ID: 1999-012.
PCT International Search Report performed by the EPO. (of-record in parent application).
International Search Report dated Jul. 24, 2007, PCT Application US2005/003753. (of-record in parent application).
Dec. 15, 2009 First Official Report for Australian Application No. 2005213459, filed Feb. 4, 2005.
Dec. 15, 2010 Second Official Report for Australian Application No. 2005213459, filed Feb. 4, 2005.
Jun. 15, 2010 Examination Report for European Application No. EP05712981, filed Feb. 4, 2005.
May 25, 2010 Notice of Reasons for Rejection for Japanese Application No. 2006-552309, filed Feb. 4, 2005.
Feb. 15, 2011 Decision of Rejection for Japanese Application No. 2006-552309, filed Feb. 4, 2005.
Feb. 15, 2011 Notice of Reasons for Rejection for Japanese Application No. 2010-221380 filed Feb. 4, 2005.
Mar. 14, 2011 Partial European Search Report for Application No. EP 10 17 8979 filed on Feb. 4, 2005 the European Counterpart of the present application.

* cited by examiner

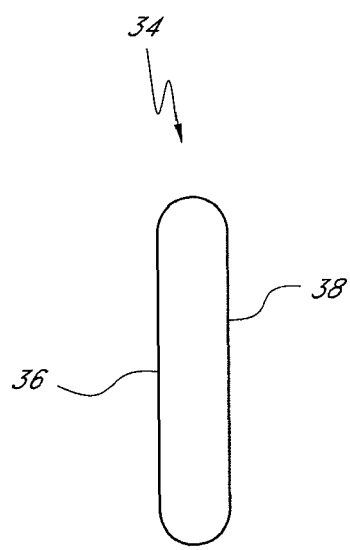 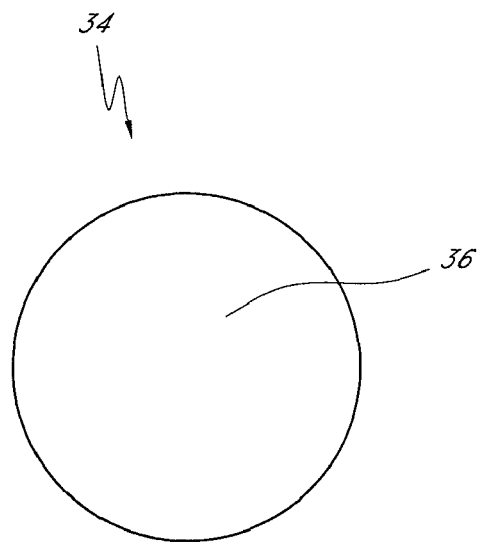
FIG. 7A  FIG. 7B
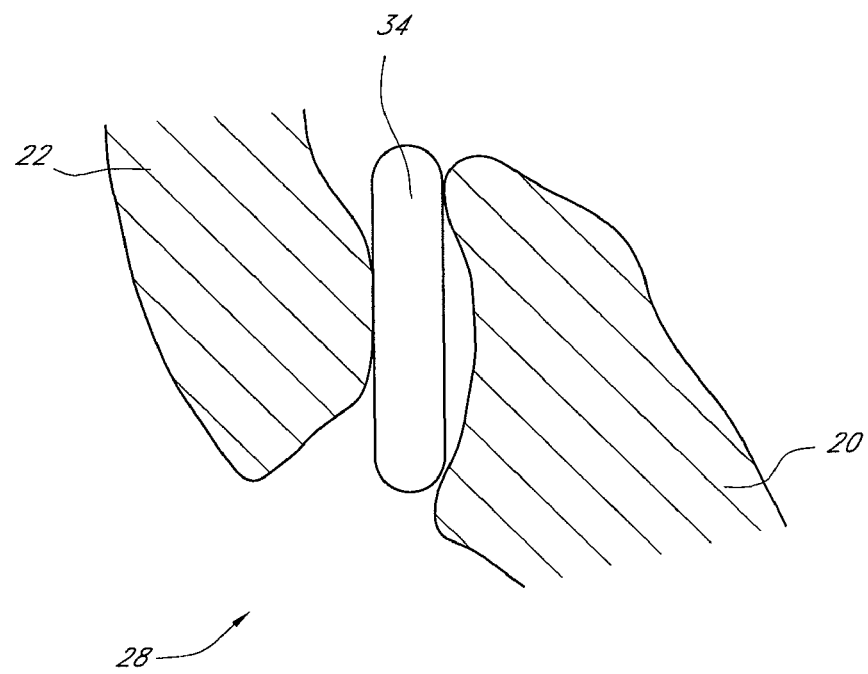
FIG. 8

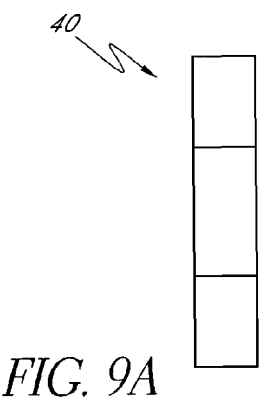
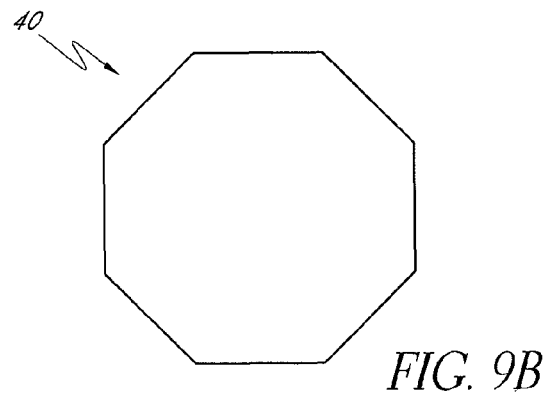
FIG. 9A    FIG. 9B
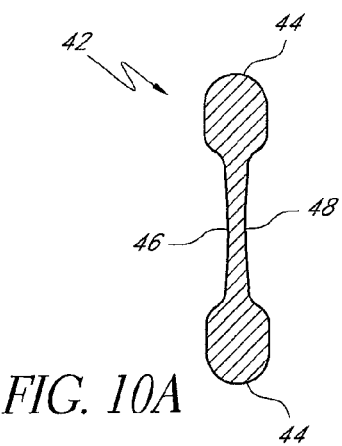
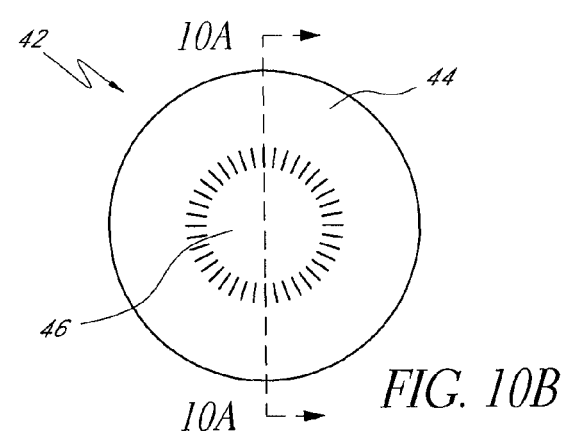
FIG. 10A    FIG. 10B
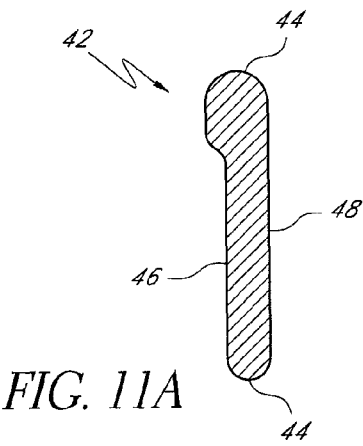
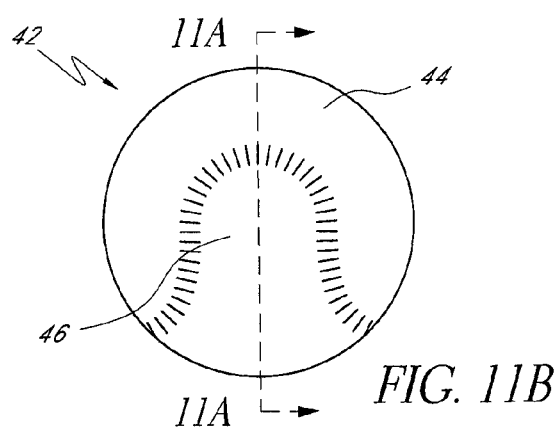
FIG. 11A    FIG. 11B

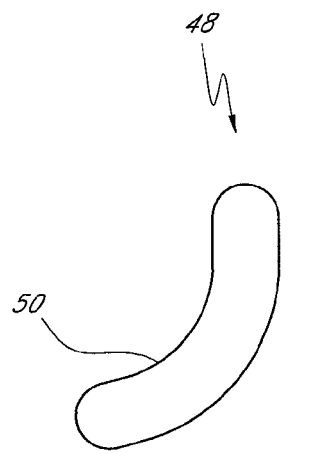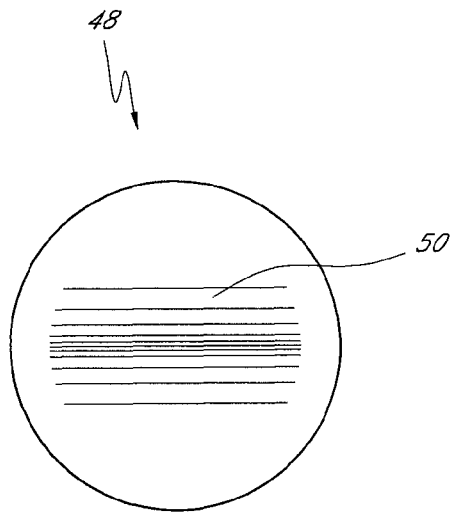
FIG. 12A   FIG. 12B
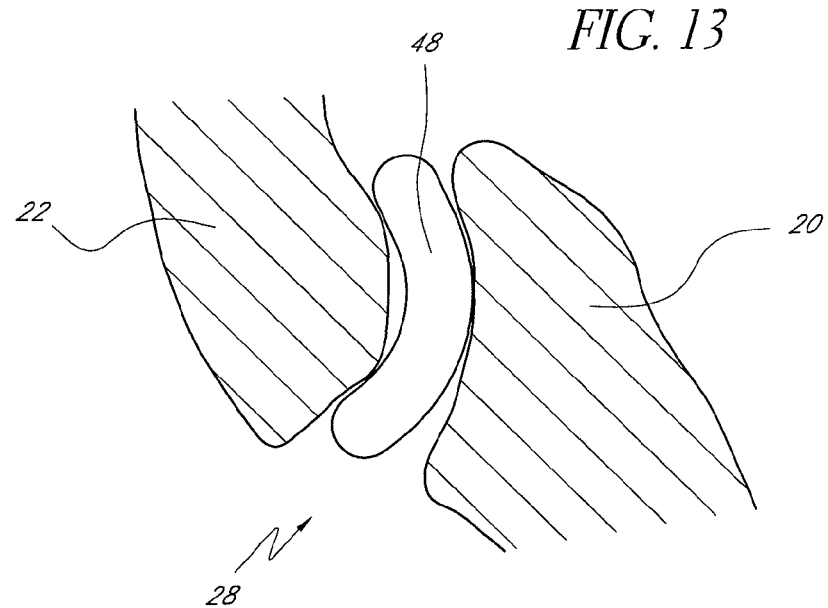
FIG. 13

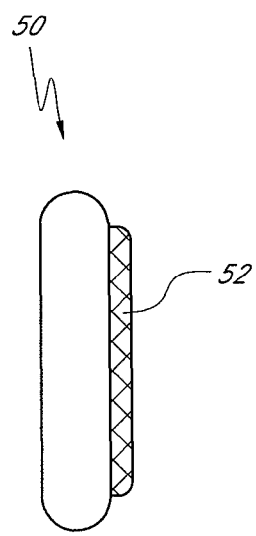 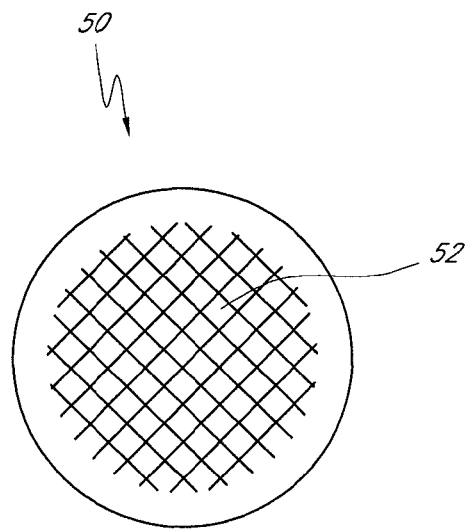
FIG. 14A  FIG. 14B
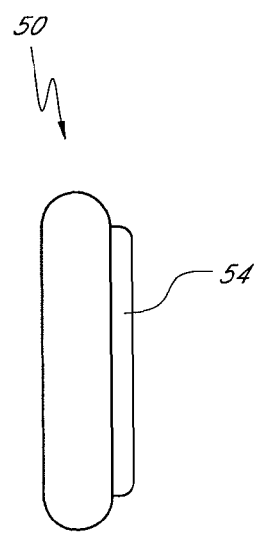 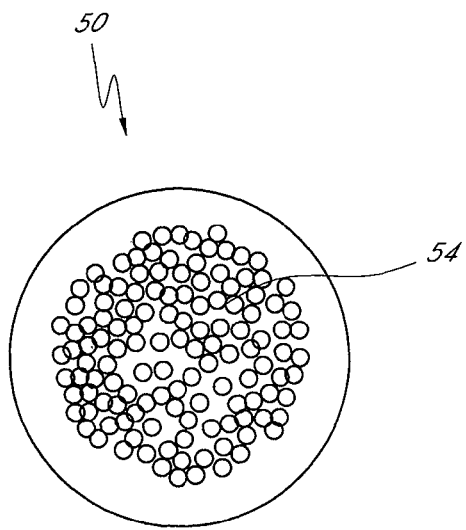
FIG. 15A  FIG. 15B

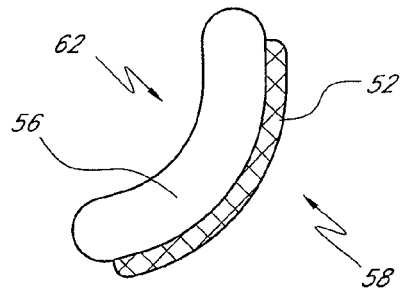
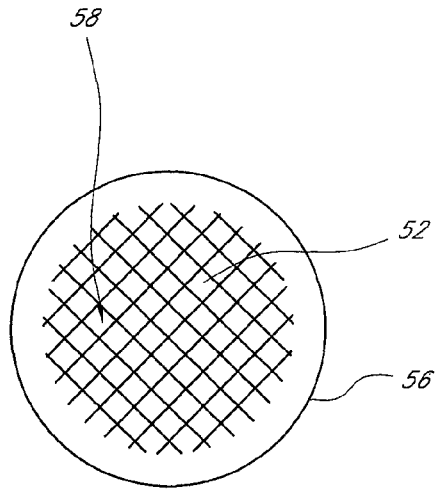
*FIG. 16A*  *FIG. 16B*
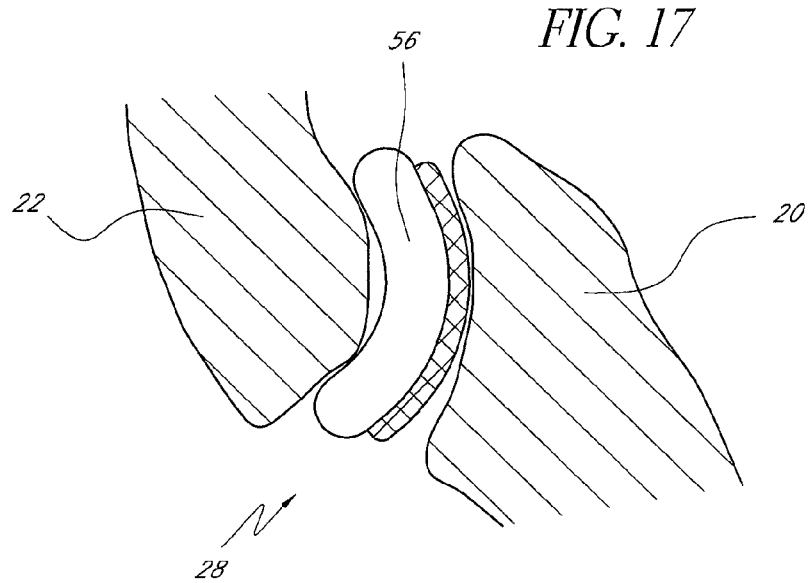
*FIG. 17*

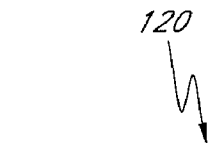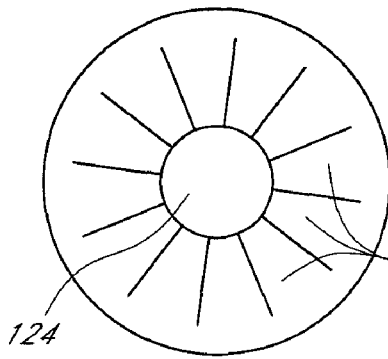
FIG. 34A    FIG. 34B
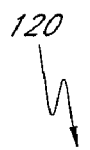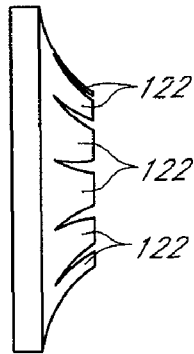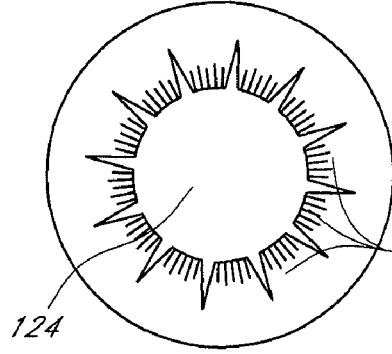
FIG. 35A    FIG. 35B

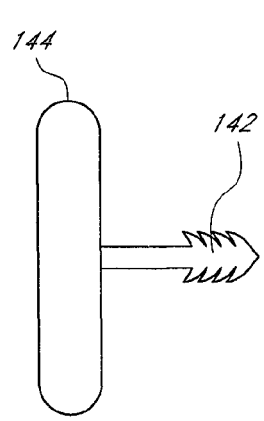
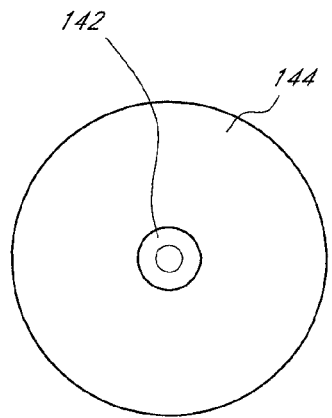
FIG. 40A                    FIG. 40B
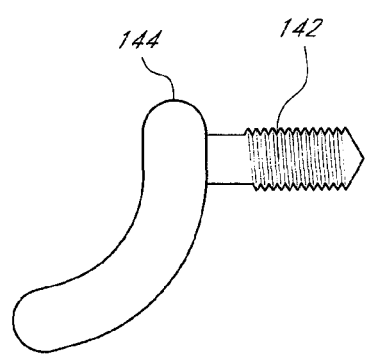
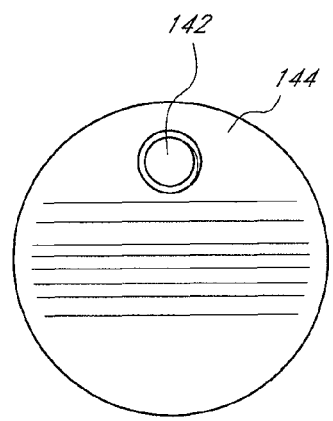
FIG. 41A                    FIG. 41B

VERTEBRAL FACET JOINT PROSTHESIS AND METHOD OF FIXATION

RELATED APPLICATION INFORMATION

This application is a divisional of U.S. patent application Ser. No. 10/865,073, filed Jun. 10, 2004, which claims the priority benefit under 35 U.S.C. §119(e) to a) U.S. Provisional Patent Application No. 60/542,351, filed Feb. 6, 2004, b) U.S. Provisional Patent Application No. 60/542,769, filed Feb. 6, 2004, and c) U.S. Provisional Patent Application No. 60/542,350, filed Feb. 6, 2004, the disclosures of which are incorporated by reference herein in their entirety.

FIELD OF THE INVENTION

The present invention relates to devices for augmentation and restoration of vertebral facet joints affected by degeneration and the surgical method of implanting these devices in the spine.

BACKGROUND OF THE INVENTION

Traumatic, inflammatory, and degenerative disorders of the spine can lead to severe pain and loss of mobility. According to some studies, back and spinal musculoskeletal impairments are the leading causes of lost work productivity in the United States. Pain as a result of some type of spinal impairment may have its source in a variety of pathologies or clinical conditions.

One source for back and spine pain is related to degeneration of the facets of the spine or facet arthritis. Bony contact or grinding of degenerated facet joint surfaces may play a role in some pain syndromes. While many technological advances have focused on the spinal disc and artificial replacement or repair of the disc, little advancement in facet repair has been made. Facet joint and disc degeneration frequently occur together. Thus, there is a need to address the clinical concerns raised by degenerative facet joints.

The current standard of care to address the degenerative problems with the facet joints is to fuse the two adjacent vertebrae together. By performing this surgical procedure, the relative motion between the two adjacent vertebrae is stopped, thus stopping motion of the facets and any potential pain generated as a result thereof. This surgical procedure has a high rate of morbidity and can potentially lead to further clinical complications such as adjacent segment disorders. This procedure is also not reversible. Therefore, if the patient has an unsatisfactory result, they maybe subject to additional surgical fusion procedures.

SUMMARY OF THE INVENTION

The present invention aims at addressing the clinical condition of the patient while allowing the patient to maintain mobility not common with fusion procedures. The device and procedure allow the restoration of the relative spacing between the facets within the facet joint, alleviating the bone on bone contact that is common in degenerative facet joints and often the source of pain generation, while allowing relative motion between the facets to continue post-operatively.

While other implants have been proposed with the objective of addressing facet degeneration by restoring motion, the subject device offers the benefit of requiring little to no bony resection in order for it to be placed within the spine. This advantage provides the opportunity for the patient to rely more on those anatomical structures unaffected by degeneration while providing for very little morbidity in the surgical procedure.

One embodiment of the invention comprises a device for treating spinal disorders while preserving movement at a facet joint. The device comprises a prosthesis having a first face and a second face, where the first face is adapted to be secured to the adjacent articular surface of a facet and the second surface is configured for sliding contact with an adjacent structure. In one embodiment, the device is dimensioned to substantially fit within a joint capsule of the facet joint and has a thickness generally equal to the normal anatomic spacing between the two facets of the facet joint. In some embodiments, the device has a curve adapted to match the natural shape of a facet and a size adapted to fit substantially within a joint capsule of the facet joint. The device may comprise at least one material selected from the group consisting of polymers, polyetheretherketone (PEEK), polyetherketoneketone (PEKK), polyethylene, fluoropolymers, hydrogels, elastomers, ceramics, zirconia, alumina, silicon nitride; metal(s), titanium, titanium alloy, cobalt chromium, stainless steel, and combinations of these materials. In one embodiment, the second face of the device comprises a highly polished surface. In one embodiment, the first face may comprise a roughened surface or a porous surface. In some embodiments, at least one face of the device is sufficiently malleable to be capable of generally conforming to the shape of an adjacent surface or structure under normal anatomical loads.

In one embodiment of the invention, a device for treating spinal disorders while preserving movement at a facet joint is provided. The device may comprise a prosthesis having a first face and a second face, where the first face is adapted for sliding contact with a first articular process of a facet joint and the second surface is configured for sliding contact with a second articular process of the facet joint. In one embodiment, the device is dimensioned to substantially fit within a joint capsule of the facet joint and has a thickness generally equal to the normal anatomic spacing between the two facets of a facet joint. In one embodiment, the device has a curve adapted to match the natural shape of a facet and a size adapted to fit substantially within a joint capsule of the facet joint. The device has a thickness approximately equal to the normal anatomic spacing between the two facets of the facet joint. In one embodiment, the device has an average thickness within the range of about 0.5 mm to about 3 mm. In one embodiment, the device has an average thickness within the range of about 1 mm to about 2 mm. In another embodiment, the device has a diameter within the range of about 5 mm to about 25 mm. In another embodiment, the device has a size within the range of about 10 mm to about 20 mm in diameter. In one embodiment, at least one face of the device has a bone contacting surface area of about 25 $mm^2$ to about 700 $mm^2$. In another embodiment, at least one face of the device has a bone contacting surface area of about 20 $mm^2$ to about 400 $mm^2$. In still another embodiment of the device, at least one face of the device has a bone contacting surface area of about 20 $mm^2$ to about 100 $mm^2$. In one embodiment, the device has at least one face comprising a highly polished surface. In some embodiments, at least one face of the device is sufficiently malleable to be capable of generally conforming to the shape of at least a portion of an articular process under normal anatomical conditions.

The prosthesis may further comprise an anchoring assembly configured to generally maintain at least a portion of the prosthesis between the first articular process and the second articular process of the facet joint. The anchoring assembly may comprise an elongate member and at least one retaining member. In one embodiment, the elongate member comprises a wire or cable. In another embodiment, the elongate member comprises a solid wire or cable. In still another embodiment, the elongate member comprises a braided cable. The retaining member may comprise a set screw retaining ring. In one embodiment, at least one end of the device comprises a threaded interface. In one embodiment, the retaining member comprises a threaded retainer. In some embodiments, the retaining member is integrally formed with one end of the elongate member.

In another embodiment of the invention, the device for treating facet joint dysfunction is provided. The device comprises a body with a first face and a second face adapted to contact the bony or cartilaginous articular surfaces of the facets of adjacent vertebrae. The device has at least one retaining interface capable of accepting an elongate retainer through it. An elongate retainer is adapted for generally maintaining the location of the body with respect to the facet joint. The retainer has a first portion adapted to engage a first facet of the facet joint and a second portion adapted to engage a second facet of the facet joint. In some embodiments of the invention, the device has a generally circular cross-section and a diameter adapted to fit substantially within a joint capsule of the facet joint. The device has a thickness generally equal to the normal anatomic spacing between the two facets of the facet joint. In still other embodiments of the device, the device has a curve adapted to match the natural shape of the facet and a size adapted to substantially fit within a joint capsule of the facet. The device may comprise at least one material selected from the group consisting of polymers, polyetheretherketone, polyetherketoneketone, polyethylene, fluoropolymers, hydrogels, elastomers, ceramics, zirconia, alumina, silicon nitride; metal(s), titanium, titanium alloy, cobalt chromium, stainless steel, and combinations of these materials. The elongate retainer may comprise a braided polymer, a braided metal, or a solid structure. In some embodiments of the invention, the elongate retainer comprises a flexibility sufficient to tie a knot in the elongate retainer. In another embodiment, at least one end of the elongate retainer has a threaded metal section adapted to accept a threaded knot. A threaded knot is provided to retain the elongate retainer against an articular process. In one embodiment of the invention, the threaded section is pressed or crimped onto the elongate retainer. The threaded section and knot may comprise titanium, titanium alloy, cobalt chromium or stainless steel. In some embodiments of the invention, the device comprises at least one face of the highly polished surface. In some embodiments, the elongate member may comprise at least one element with an enlarged cross-sectional area. The elongate member may comprise at least one end of with a bulbous retainer, a flared retainer, a T-bar retainer or an integral ring retainer. In some embodiments, at least one face of the device is sufficiently malleable to be capable of generally conforming to the shape of at least a portion of an articular surface.

In one embodiment of the invention, a prosthesis for treating facet joint dysfunction is provided. The prosthesis comprises a body with a first face and a second face, where at least one face adapted for sliding contact with the bony or cartilaginous articular surfaces of the facets of adjacent vertebrae or the prosthesis has at least one retaining interface capable of accepting a retainer member. The retaining member is adapted for securing the location of the body with respect to at least of the articular surfaces. The retaining member may comprise a first portion adapted to engage the retaining interface of the body and a second portion adapted to engage a first facet of the facet joint. The retainer may further comprise a third portion adapted to engage a second facet of the facet joint. In one embodiment, the retainer comprises a threaded shaft and a retaining interface of the body comprises a threaded hole with an opening on one face of the body. The retaining member may also comprise a projection extending from the body. In still another embodiment, the retaining member comprises a longitudinal member adapted to engage the retaining interface of the body and at least one retainer being capable of engaging the longitudinal member. The retaining ring may comprise a set screw retaining ring. The set screw of the retaining member may have a blunted tip, curved tip, or piercing tip. Alternatively, at least one of the retaining rings may be a friction fit retaining ring. The body of the prosthesis may be curved. The prosthesis may comprise at least one material selected from the group consisting of polymers, polyetheretherketone, polyetherketoneketone, polyethylene, fluoropolymers, hydrogels, elastomers, ceramics, zirconia, alumina, silicon nitride; metal(s), titanium, titanium alloy, cobalt chromium, stainless steel, and combinations of these materials. In some embodiments, at least one face of the prosthesis is sufficiently malleable to be capable of generally conforming to the shape of at least a portion of an articular surface.

In one embodiment, a prosthesis for treating facet joint dysfunction is provided. The prosthesis comprises a first body with a first face and a second face and a second body within a first face and a second face. The first face of each body is adapted to articulate with the first face of the other body and the second face of each body is adapted to engage a facet of a facet joint. The prosthesis may further comprise a retaining member adapted for securing a location of at least one body. In some embodiments, at least one face of the prosthesis is sufficiently malleable to be capable of generally conforming to the shape of at least a portion of an articular surface.

In another embodiment of the invention, a method for treating vertebral dysfunction is provided. This method comprises opening a facet joint capsule between two facets of adjacent vertebral bodies, distracting the adjacent vertebral bodies from a first spacing to a second spacing and placing the spacer between the two facets to maintain the second spacing. The method may further comprise the steps of securing the spacer to one facet of the facet joint. The method may also comprise securing the spacer in the facet joint capsule. The step of securing the spacer may comprise drilling a hole through each facet, threading a retainer through the hole of the first facet, threading the retainer through the hole in the spacer, threading the retainer through the hole of the second facet, and tying a knot in at least one end of the retainer. The method may further comprise the steps of drilling a hole through a first facet and a second facet, advancing the retainer through the hole of the first facet, advancing the retainer through the hole in the spacer, threading the retainer through the hole of the second facet and threadably engaging an anchor to at least one end of the retainer. The step of securing the spacer may further comprise providing a spacer with a retaining member and advancing the retaining member at least partially into a facet to engage the facet. The method may also further comprise the step of conforming the shape of at least a portion of the spacer to at least a portion of a facet of the facet joint. In a further embodiment, the conforming step is performed after the placing step. In another embodiment, the conforming step is performed while the spacer is generally located between the facets of the facet joint.

In another embodiment of the invention, a method of treating the facet joint is provided. The method comprises providing a prosthesis dimension to fit within a facet joint capsule, accessing a facet joint capsule between two articular prosthesis of two vertebrae, inserting a prosthesis generally within the joint capsule and maintaining the prosthesis generally between the two articular prosthesis without penetrating the surface of a vertebrae. Maintaining the prosthesis may comprise anchoring the prosthesis to the joint capsule tissue, or generally closing the joint capsule over the prosthesis. The prosthesis can also be maintained between the articular prosthesis by suturing the prosthesis to the surrounding soft tissue. The method may also further comprise the step of conforming the shape of at least a portion of the prosthesis to at least a portion of a facet of the facet joint. In a further embodiment, the conforming step is performed after the inserting step. In another embodiment, the conforming step is performed while the prosthesis is generally located between the facets of the facet joint.

BRIEF DESCRIPTION OF THE DRAWINGS

The structure and operation of the invention will be better understood with the following detailed description of embodiments of the invention, along with the accompanying illustrations, in which:

FIGS. 7A and 7B are schematic views of one embodiment of a facet joint prosthesis comprising a circular disc;

FIG. 8 is a schematic view of the prosthesis from FIG. 7A implanted in a facet joint;

FIGS. 9A and 9B are schematic views of one embodiment of a facet joint prosthesis comprising an octagonal disc;

FIGS. 10A and 10B are schematic views of one embodiment of a facet joint prosthesis comprising a biconcave disc;

FIGS. 11A and 11B are schematic views of one embodiment of a facet joint prosthesis comprising a single-face variable thickness disc;

FIGS. 12A and 12B are schematic views of one embodiment of a facet joint prosthesis comprising a curved disc;

FIG. 13 is a schematic view of the prosthesis from FIG. 12A implanted in a facet joint;

FIGS. 14A and 14B are schematic views of one embodiment of a facet joint prosthesis comprising a disc with a roughened surface on one face;

FIGS. 15A and 15B are schematic views of one embodiment of a facet joint prosthesis comprising a disc with a porous surface on one face;

FIGS. 16A and 16B are schematic views of one embodiment of a facet joint prosthesis comprising a bent disc with a roughened surface on the greater face;

FIG. 17 is a schematic view of the prosthesis from FIG. 16A implanted in a facet joint;

FIGS. 34A to 35B are one embodiment of the invention comprising friction fit retaining rings. FIGS. 34A and 34B depict the retaining rings in their reduced state and FIGS. 35A and 35B depict the retaining rings in their expanded state;

FIGS. 36B and 36C depict a threaded retaining member with a pivotable washer;

FIGS. 40A and 40B are schematic views of one embodiment of a facet joint prosthesis with an integral retaining member comprising a centrally located barbed spike;

FIGS. 41A and 41B are schematic views of one embodiment of a facet joint prosthesis with an integral retaining member comprising an eccentrically located barbed spike;

FIGS. 51A to 51C are posterior views of the surgical procedure and FIGS. 51D and 51E are cross sectional views of the surgical procedure.

DETAILED DESCRIPTION OF THE PREFERRED EMBODIMENT

A. Anatomy of the Spine

Figure 1:
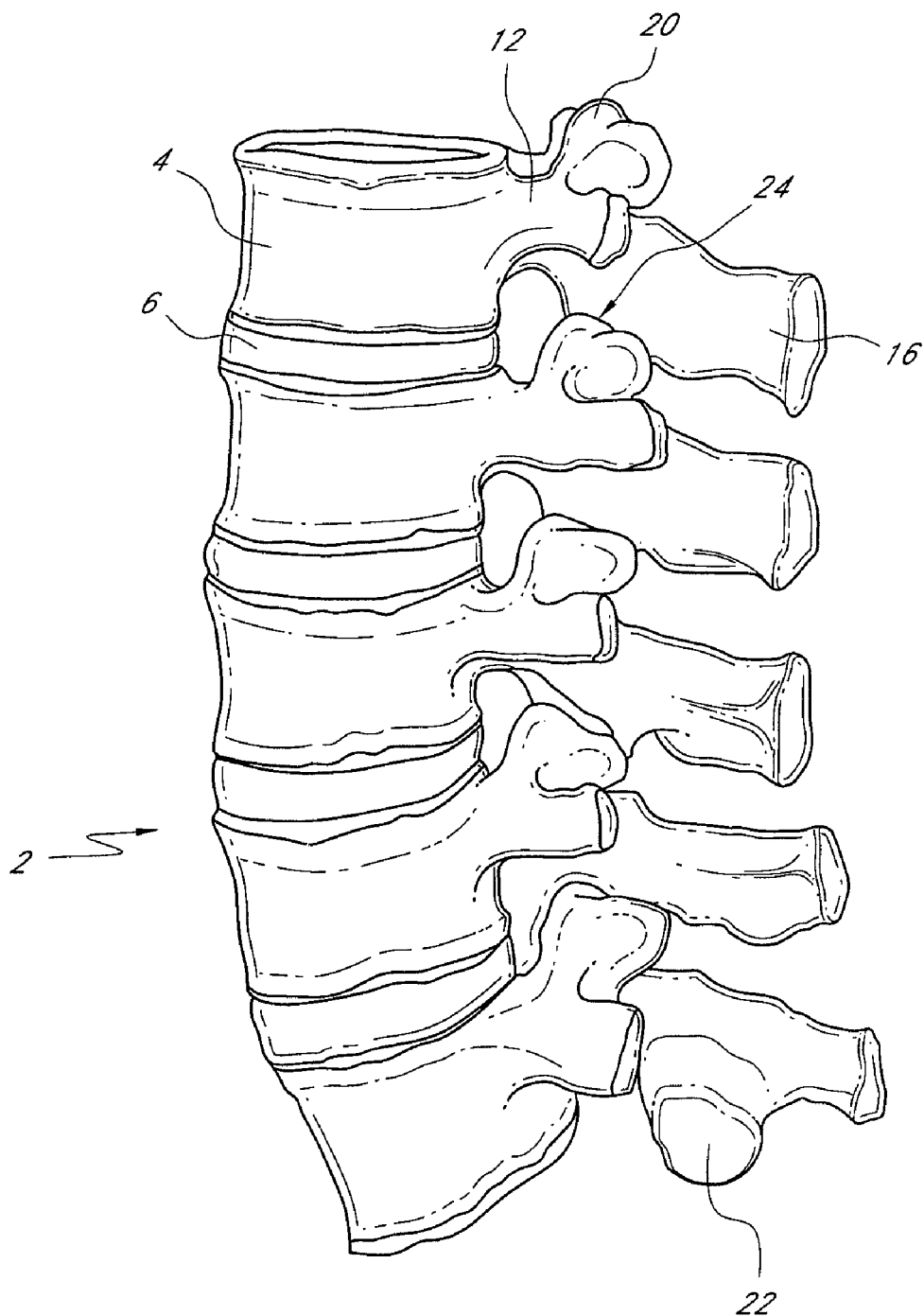
FIG. 1 is a lateral elevational view of a portion of the vertebral column.
Figure 2A:
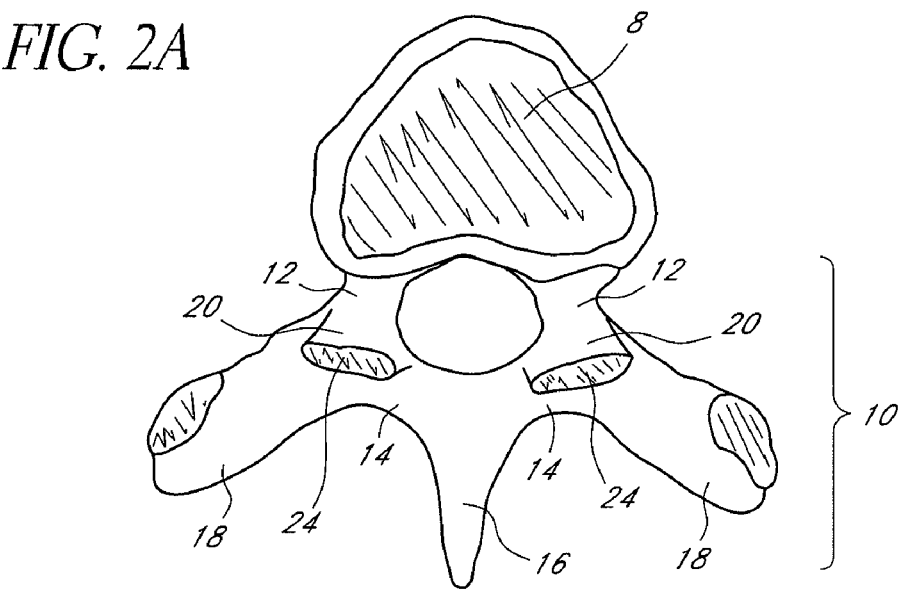
FIGS. 2A and 2B are schematic superior and side views of an isolated thoracic vertebra.
Figure 2B:
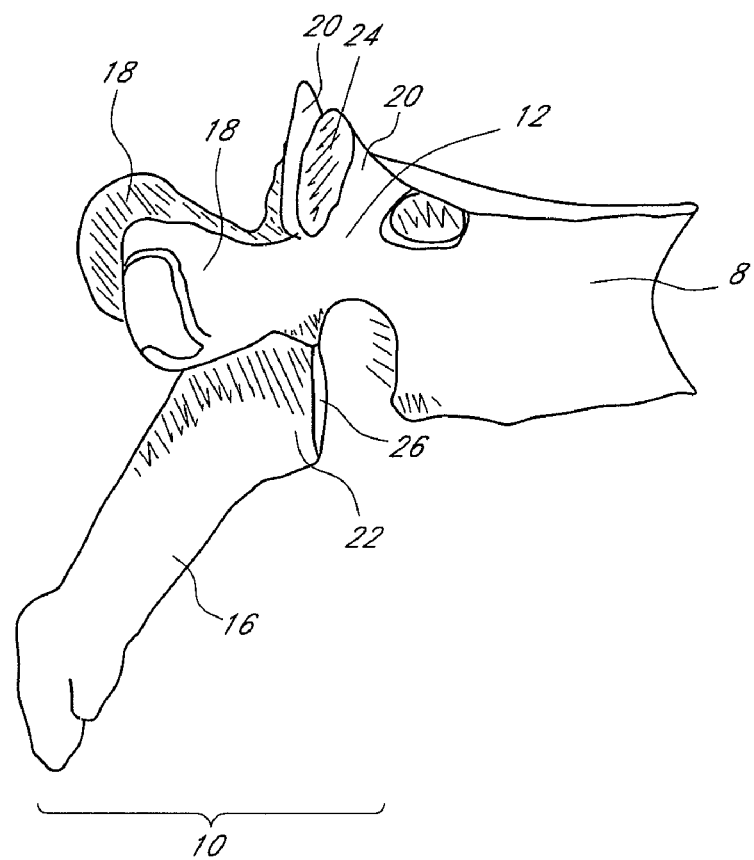
Figure 3A:
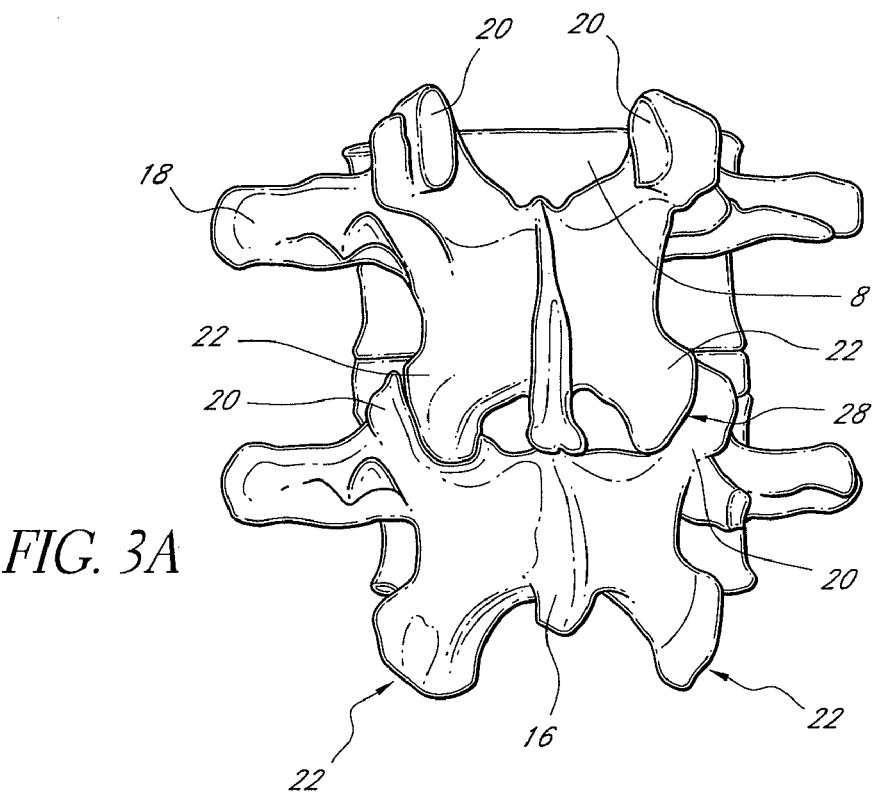
FIGS. 3A and 3B are schematic posterior and posterior-oblique elevational views of a portion of the vertebral column.
Figure 3B:
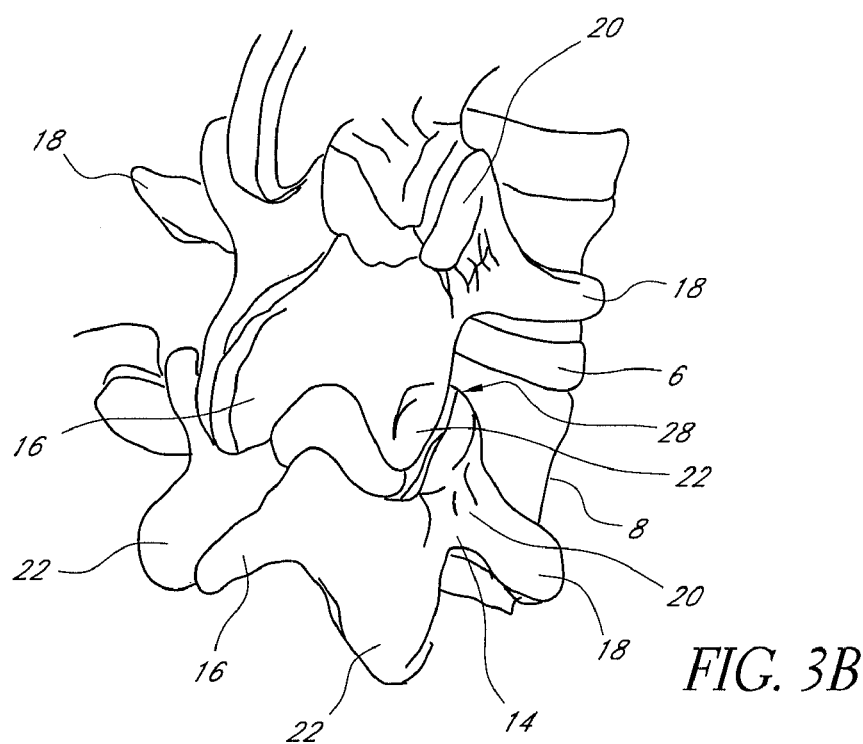
Figure 4A:
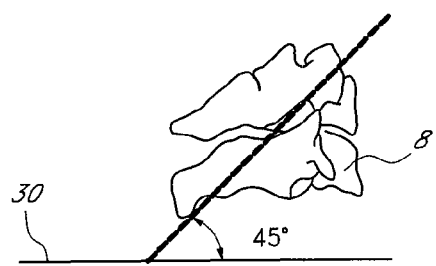
FIGS. 4A and 4B are schematic side and superior views of a facet joint in the cervical vertebrae.
Figure 4B:
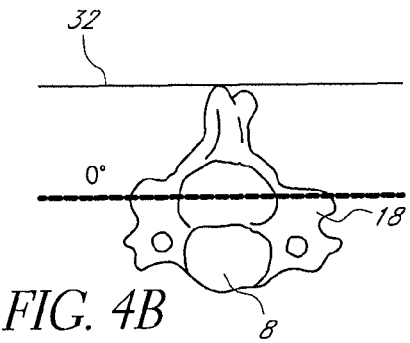

As shown in FIG. 1, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 comprises two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28 with the articular processes of the adjacent vertebrae. See FIGS. 3A and 3B. The facet joints are true synovial joints with cartilaginous surfaces and a joint capsule.

Figure 5A:
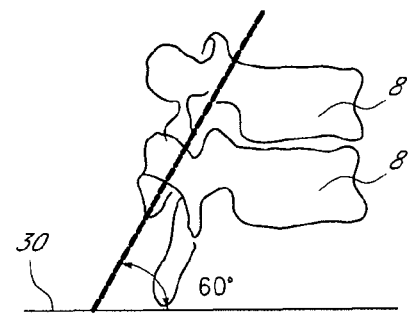
FIGS. 5A and 5B are schematic side and superior views of a facet joint in the thoracic vertebrae.
Figure 5B:
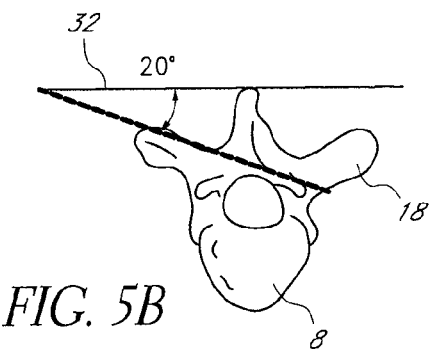
Figure 6A:
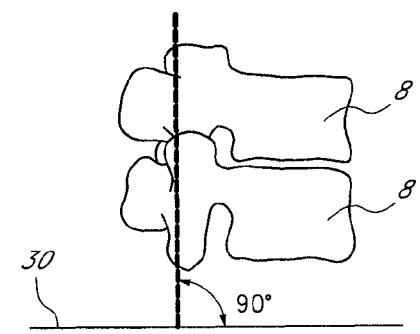
FIGS. 6A and 6B are schematic side and superior views of a facet joint in the lumbar vertebrae.
Figure 6B:
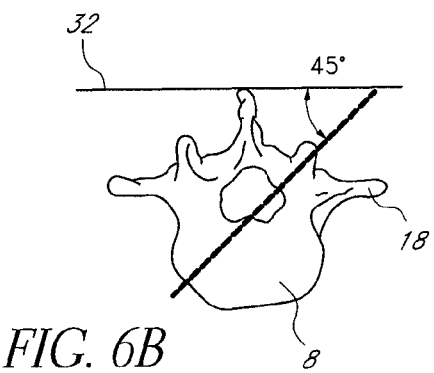

The orientation of the facet joints vary, depending on the level of the vertebral column. In the C1 and C2 vertebrae, the facet joints are parallel to the transverse plane. FIGS. 4A to 6B depict the orientations of the facet joints at different levels of the vertebral column. In the C3 to C7 vertebrae shown in FIGS. 4A and 4B, the facets are oriented at a 45-degree angle to the transverse plane 30 and parallel to the frontal plane 32, respectively. This orientation allows the facet joints of the cervical vertebrae to flex, extend, lateral flex and rotate. At a 45-degree angle in the transverse plane 30, the facet joints of the cervical spine can guide, but do not limit, the movement of the cervical vertebrae. FIGS. 5A and 5B depict the thoracic vertebrae, where the facets are oriented at a 60-degree angle to the transverse plane 30 and a 20-degree angle to the frontal plane 32, respectively. This orientation is capable of providing lateral flexion and rotation, but only limited flexion and extension. FIGS. 6A and 6B illustrate the lumbar region, where the facet joints are oriented at 90-degree angles to the transverse plane 30 and a 45-degree angle to the frontal plane 32, respectively. The lumbar vertebrae are capable of flexion, extension and lateral flexion, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. One study by King et al. *Mechanism of Spinal Injury Due to Caudocephalad Acceleration, Orthop. Clin. North Am.,* 6:19 1975, found facet joint load-bearing as high as 30% in some positions of the vertebral column. The facet joints may also play a role in resisting shear stresses between the vertebrae. Over time, these forces acting on the facet joints can cause degeneration and arthritis.

B. Joint Prosthesis

In one embodiment of the invention, a device for restoring the spacing between two facets of a facet joint is provided. As shown in FIGS. 7A and 7B, the device comprises a prosthesis 34 with a least two faces, a first face 36 adapted to contact the articular surface of one facet of the facet joint and a second face 38 adapted to contact the articular surface of the other facet. In one embodiment, the prosthesis 34 has a generally circular profile and is sized to fit generally within the joint capsule of the facet joint 28. FIG. 8 illustrates the prosthesis 34 of FIGS. 7A and 7B positioned in a facet joint. In other embodiment of the invention, the prosthesis can have any of a variety of profiles, including but not limited to square, rectangle, oval, star, polygon or combination thereof. An octagonal prosthesis is shown in FIGS. 9A and 9B. In one embodiment of the invention, a prosthesis having the desired shape is selected from an array of prostheses after radiographic visualization of the articular processes and/or by radio-contract injection into the facet joint to visualize the joint capsule. In one embodiment, the prosthesis has a diameter of about 4 mm to about 30 mm. In another embodiment, the prosthesis has a diameter of about 5 mm to about 25 mm. In still another embodiment, the prosthesis has a diameter of about 10 mm to about 20 mm. In one embodiment, the prosthesis has a cross-sectional area of about 10 mm$^2$ to about 700 mm$^2$. In another embodiment, the prosthesis has a cross-sectional area of about 25 mm$^2$ to about 500 mm$^2$. In still another embodiment, the prosthesis has a cross-sectional area of about 20 mm$^2$ to about 400 mm$^2$, and preferably about 25 mm$^2$ to about 100 mm$^2$.

The prosthesis has a thickness generally equal to about the anatomic spacing between two facets of a facet joint. The prosthesis generally has a thickness within the range of about 0.5 mm to about 3.0 mm. In certain embodiments, the prosthesis has a thickness of about 1 mm to about 2 mm. In one preferred embodiment, the prosthesis has a thickness of about 0.5 mm to about 1.5 mm. In one embodiment, the thickness of the prosthesis is nonuniform within the same prosthesis. For example, in FIGS. 10A and 10B, the thickness of the prosthesis 42 is increased around the entire outer edge 44, along at least one and, as illustrated, both faces 46, 48. In FIGS. 11A and 11B, only a portion of the edge 44 on one face 46 of the prosthesis 42 has a thickness that is greater than the thickness of a central region, and, optionally, also thicker than the typical anatomic spacing between two facets of a facet joint. An increased edge thickness may resist lateral displacement of the prosthesis out of the facet joint.

In some embodiments of the invention, the prosthesis is configured to provide an improved fit with the articular process and/or joint capsule. For example, in FIGS. 12A and 12B, the prosthesis 49 has a bend, angle or curve 50 to generally match the natural shape of an articular facet. FIG. 13 depicts the prosthesis of FIGS. 12A and 12B positioned in a facet joint. The prosthesis may be rigid with a preformed bend. Alternatively, the prosthesis may be sufficiently malleable that it will conform post implantation to the unique configuration of the adjacent facet face. Certain embodiments of the invention, such as those depicted in FIG. 8 and FIG. 13, the prosthesis is configured to be implanted between the articular processes and/or within the joint capsule of the facet joint, without securing of the prosthesis to any bony structures. Such embodiments can thus be used without invasion or disruption of the vertebral bone and/or structure, thereby maintaining the integrity of the vertebral bone and/or structure.

In one embodiment, at least a portion of one surface of the prosthesis is highly polished. A highly polished portion of the prosthesis may reduce the surface friction and/or wear in that portion of the prosthesis as it contacts bone, cartilage or another surface of the prosthesis. A highly polished surface on the prosthesis may also decrease the risk of the prosthesis wedging between the articular surfaces of the facet joint, which can cause pain and locking of the facet joint.

In one embodiment, shown in FIGS. 14A and 14B, at least a portion of one surface of the prosthesis 50 has a roughened surface 52. A roughened surface may be advantageous when in contact with a bone or tissue surface because it may prevent slippage of the prosthesis 50 against the bone and aid in maintaining the prosthesis 50 in the joint. In one embodiment of the invention, shown in FIGS. 15A and 15B, at least a portion of one surface of the prosthesis 50 has a porous surface 54. A porous surface 54 can be created in any a variety of ways known in the art, such as by applying sintered beads or spraying plasma onto the prosthesis surface. A porous surface 54 can allow bone to grow into or attach to the surface of the prosthesis 50, thus securing the prosthesis 50 to the bone. In one embodiment, an adhesive or sealant, such as a cyanoacrylate, polymethylmethacrylate, or other adhesive known in the art, is used to bond one face of the prosthesis to an articular surface.

In one embodiment of the invention, one surface of the prosthesis is roughened or porous and a second surface that is highly polished. The first surface contacts or engages one facet of the facet joint and aids in maintaining the prosthesis between the articular surfaces. The second surface of the prosthesis is highly polished and contacts the other facet of the facet joint to provide movement at that facet joint. FIGS. 16A and 16B represent one embodiment of the prosthesis comprising a curved or bent disc 56 with a roughened surface 52 on the greater face 58 of the disc and a highly polished surface 60 on the lesser face 62. FIG. 17 depicts the prosthesis of FIGS. 16A and 16B positioned in a facet joint. The prosthesis generally maintains a fixed position relative to the facet contacting the roughened surface while the movement of the facet joint is preserved between the other facet and the highly polished lesser face of the prosthesis.

Figure 18A:
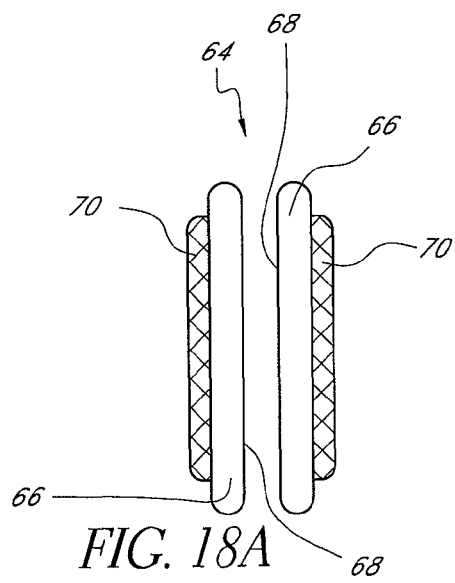
FIGS. 18A and 18B are schematic views of one embodiment of a facet joint prosthesis comprising two discs, each with a roughened surface on one face.
Figure 18B:
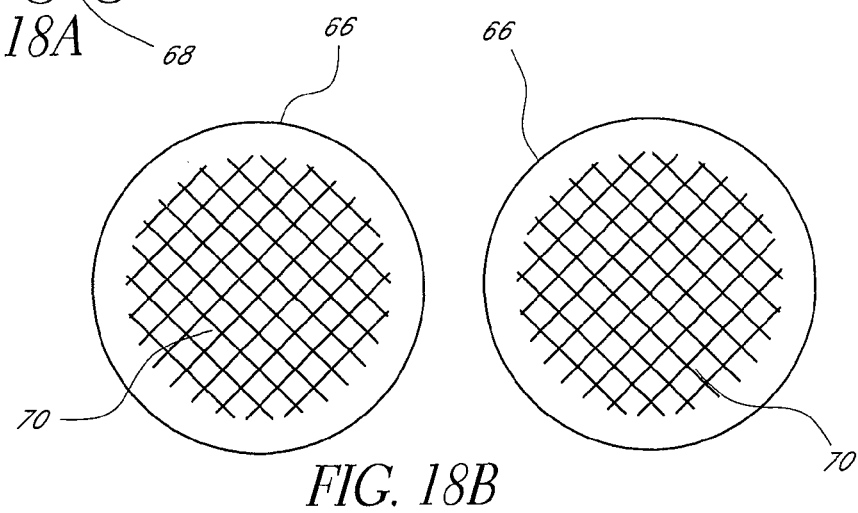
Figure 19:
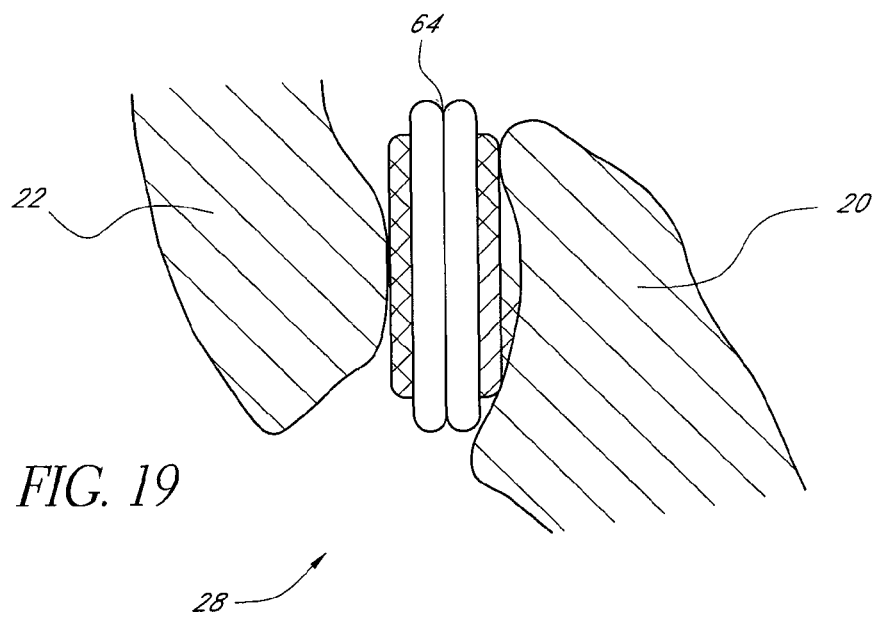
FIG. 19 is a schematic view of the prosthesis from FIG. 18A implanted in a facet joint.

FIGS. 18A and 18B show one embodiment of the invention, where the prosthesis 64 comprises two separate discs 66, each disc comprising a first face 68 that articulates with the complementary first face 68 of the other disc, and a second face 70 adapted to secure the disc to the adjacent bone or cartilage of one facet of the facet joint 28. In one embodiment of the invention, the thickness of one disc will generally be about half of the anatomic spacing between two facets of the facet joint. In other embodiments of the invention, the prosthesis comprises three or more discs. In one embodiment the total thickness of all the discs is generally about 25% to about 300% of the anatomic spacing between the two facets. In another embodiment, the total thickness of the discs is generally about 50% to about 150% of the anatomic spacing. In still another embodiment, the total thickness of the discs is about 75% to about 125% of the anatomic spacing. Each disc of the two-part prosthesis can otherwise also have features similar to those of a single-disc prosthesis, including but not limited to curved or bent configurations, highly polished or roughened surfaces, and other feature mentioned below. The two discs need not have the same size, thickness, configuration or features. FIG. 19 depicts one embodiment of a two-part prosthesis 64 positioned within a facet joint 28.

The prosthesis can be manufactured from any of a variety of materials known in the art, including but not limited to a polymer such as polyetheretherketone (PEEK), polyetherketoneketone (PEKK), polyethylene, fluoropolymer, hydrogel, or elastomer; a ceramic such as zirconia, alumina, or silicon nitride; a metal such as titanium, titanium alloy, cobalt chromium or stainless steel; or any combination of the above materials.

C. Prosthesis with a Retaining Configuration

In one embodiment of the invention, the prosthesis is maintained between the two facets of the facet joint by taking advantage of the joint capsule and/or other body tissue surrounding the facet joint to limit the migration of the prosthesis out of the facet joint. In some embodiments of the invention, the shape of the prosthesis itself is capable of resisting displacement of the prosthesis from its position generally between the facet joint surfaces. In one embodiment, a concave or biconcave configuration resists displacement of the prosthesis by providing an increased thickness at the periphery of the prosthesis that requires a larger force and/or greater distraction of facet joint surfaces in order to cause displacement. In other embodiments, surface treatments or texturing are used to maintain the prosthesis against a facet of the facet joint, as described previously. In some embodiments, a combination of disc configuration, surface texturing and existing body tissue or structures are used to maintain the position of the prosthesis.

Bone growth facilitators, electrical current, or other known techniques may be used to accelerate osteoincorporation of textured or microporous anchoring surfaces.

D. Prosthesis with a Retaining Member

The prosthesis may be configured with a retaining interface to engage a retaining member that facilitates retention of the prosthesis within the joint capsule of the facet joint. Use of a retaining member may be advantageous for preventing migration of the prosthesis over time use or with the extreme ranges of vertebral movement that may distract the articular surfaces sufficiently to allow the prosthesis to slip out.

1. Wire/Cable Retaining Member

Figure 20:
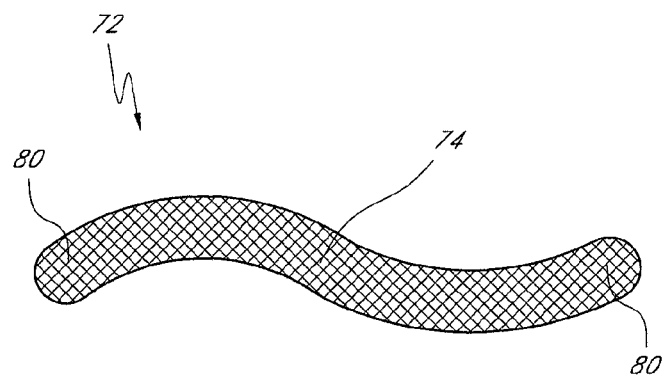
FIG. 20 is a schematic view of a retaining member comprising a braided cable.
Figures 21A, 21B:
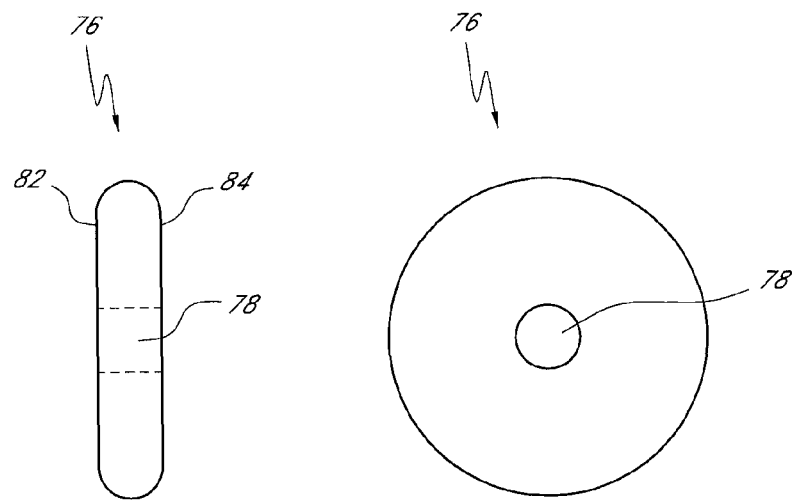
FIGS. 21A and 21B are schematic views of one embodiment of a facet joint prosthesis with a retaining interface comprising a centrally located hole.

In one embodiment of the invention, shown in FIGS. 20 to 21B, the retaining member comprises a wire or cable 72 with a portion 74 that engages the prosthesis 76 at a retaining interface 78, and at least one other portion 80 that engages or anchors to the bone or soft tissue surrounding the facet joint. The wire or cable may be solid, braided or multi-filamented. The retaining member in this embodiment will be described primarily as a cable or wire, but it is to be understood that any of a variety of elongate structures capable of extending through a central aperture will also work, including pins, screws, and single strand or multistrand polymeric strings or weaves, polymeric meshes and fabric and other structures that will be apparent to those of skill in the art in view of the disclosure herein.

The cross-sectional shape of the retaining member can be any of a variety of shapes, including but not limited to circles, ovals, squares, rectangles, other polygons or any other shape. The wire or cable generally has a diameter of about 0.5 mm to about 2 mm and a length of about 5 mm to about 60 mm. In another embodiment, wire or cable has a diameter of about 0.25 mm to about 1 mm, and preferably about 0.75 mm to about 1.25 mm. The diameter of the wire or cable may vary along the length of the wire or cable. In one embodiment, the wire or cable has a length of about 10 mm to about 40 mm. In another embodiment, the wire or cable has a length of about 20 mm to about 30 mm.

In one embodiment, shown in FIGS. 21A and 21B, the retaining interface 78 of the prosthesis 76 is a conduit between the two faces 82, 84 of the prosthesis 76, forming an aperture 78. In one embodiment, the aperture 78 has a diameter larger than the diameter of the wire or cable 72, to provide the prosthesis 76 with a range of motion as the facet joint moves. The aperture 78 inside diameter may be at least about 110%, often at least about 150% and in certain embodiments at least about 200% or 300% or greater of the outside diameter or corresponding dimension of the retaining member in the vicinity of the engagement portion 78. The cross-sectional shape of the aperture 78 can match or not match the cross sectional shape of the wire or cable used.

Figure 22A:
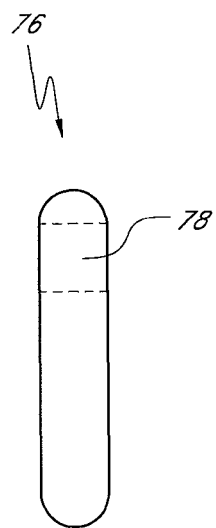
FIGS. 22A and 22B are schematic views of one embodiment of a facet joint prosthesis with a retaining interface comprising an eccentrically located hole.
Figure 22B:
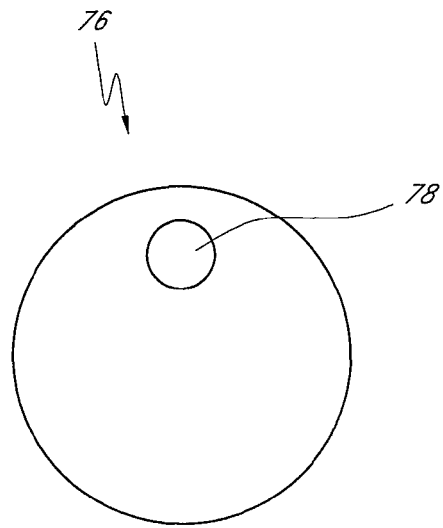
Figure 23A:
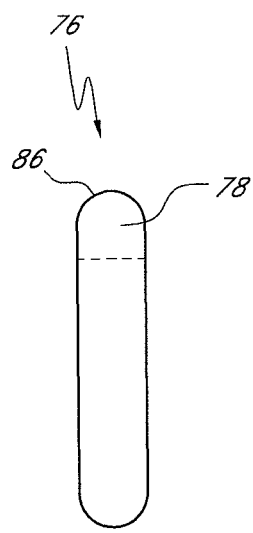
FIGS. 23A and 23B are schematic views of one embodiment of a facet joint prosthesis with a retaining interface comprising an edge contiguous hole.
Figure 23B:
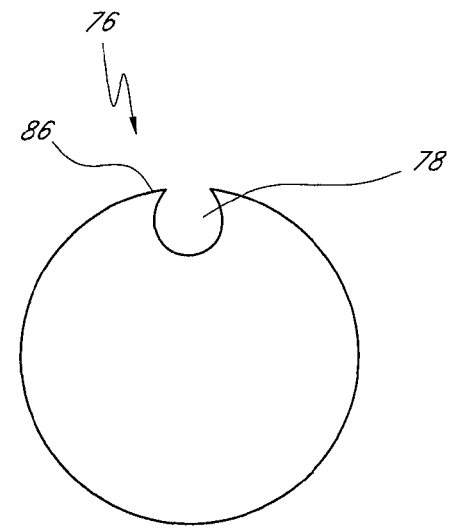
Figure 24A:
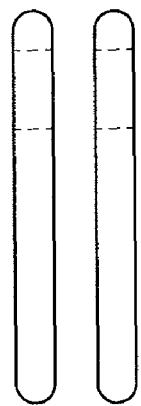
FIGS. 24A and 24B are schematic views of one embodiment of a facet joint prosthesis comprising two discs, each with an eccentrically located hole.
Figure 24B:
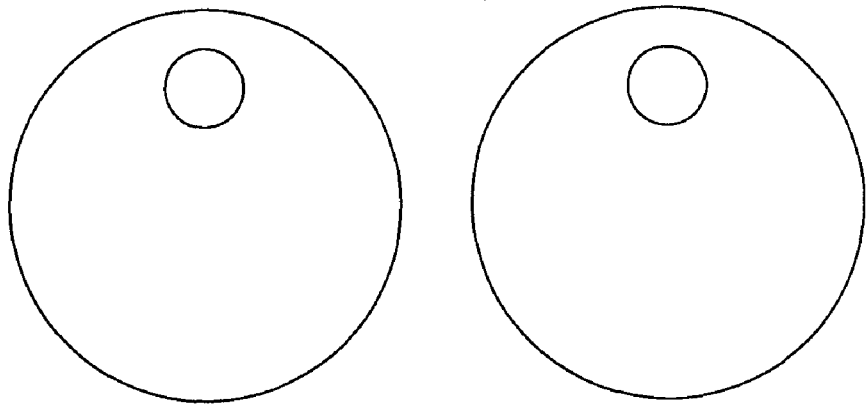
Figure 25A:
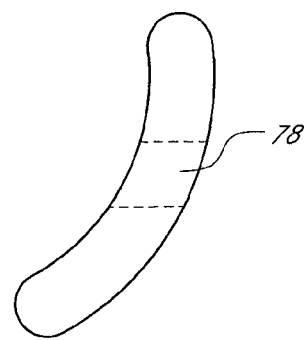
FIGS. 25A and 25B are schematic views of one embodiment of a facet joint prosthesis comprising a curved disc with a retaining interface.
Figure 25B:
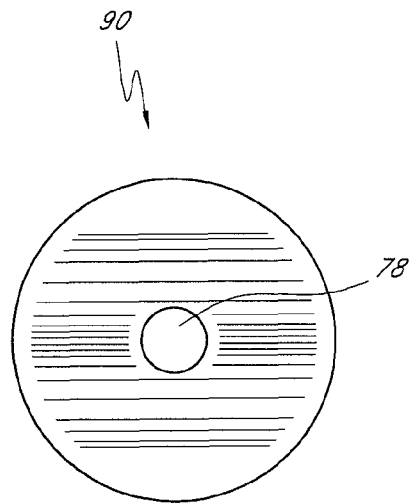

In another embodiment, the retaining interface 78 extends only partially through the prosthesis 72. The retaining interface 78 may be located generally in the center of the prosthesis, or it may be located eccentrically, as depicted in FIGS. 22A and 22B. In one embodiment, shown in FIGS. 23A and 23B, the retaining interface 78 is located at the edge 86 of the prosthesis 76 such that the interior surface of the hole 78 is contiguous with the outer edge of the prosthesis. This configuration of the retaining interface 78 does not require the cable 72 to be threaded through the retaining interface 78 and may facilitate engagement of the retaining member with the prosthesis. FIGS. 24A and 24B depict an embodiment of the invention comprising a two-part prosthesis 88. Either a single cable or two separate cables may be used retain both discs within the facet joint. FIGS. 25A and 25B depict another embodiment of the invention comprising a curved prosthesis 90 with a retaining interface 78 adapted to accept a cable.

Figure 26:
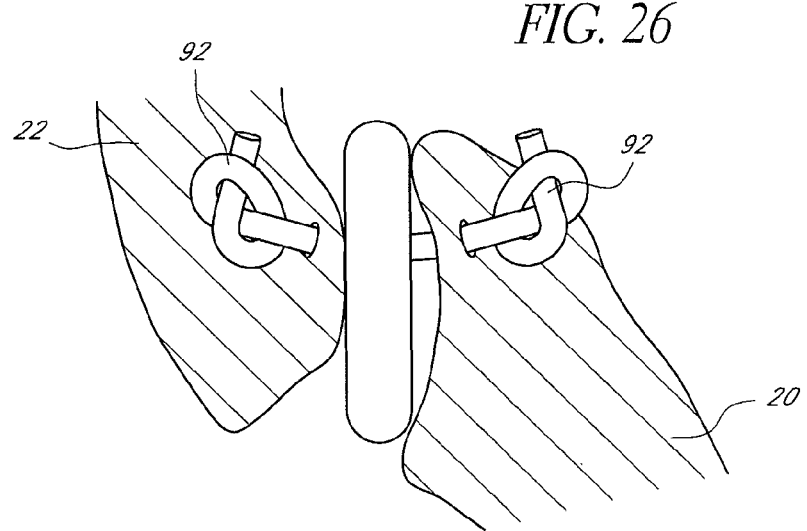
FIG. 26 depicts one embodiment of the invention where the cable is engaged to the articular processes using knots in the cable.
Figure 27A:
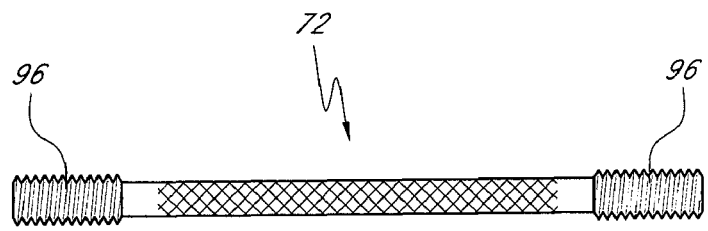
FIGS. 27A and 27B depict another embodiment of the retaining member comprising a braided cable with threaded ends adapted to accept threaded nuts.
Figure 27B:
Figure 28:
FIG. 28 depicts one embodiment of the invention where a cable is engaged to the articular processes using nuts threaded onto the cable.

In FIG. 26, the wire or cable 72 is secured to the articular processes 20, 22 by tying one or more knots 92 in the cable 72 that can resist pulling of the wire or cable through the articular process. In another embodiment, one or both ends of the wire or cable are provided with an anchor to resist migration of the implants. As shown in FIGS. 27A and 27B, one or both ends of the wire or cable 72 may be threaded such that a nut 94 can be tightened on the wire or cable 72 to secure the wire or cable to the articular processes 20, 22. FIG. 28 depicts the attachment of a nut onto a threaded end of a cable. The threaded portion 96 of the wire or cable can be secured to the cable by pressing, crimping or twisting the threaded 96 portion onto the cable 72. In one embodiment, the threaded portion 96 is made from titanium, titanium alloy, cobalt chromium, stainless steel, or any combination thereof.

In one embodiment, the wire or cable has two threaded ends 96 for engaging the bony or cartilaginous tissue, one portion for each facet of the facet joint.

Figure 29:
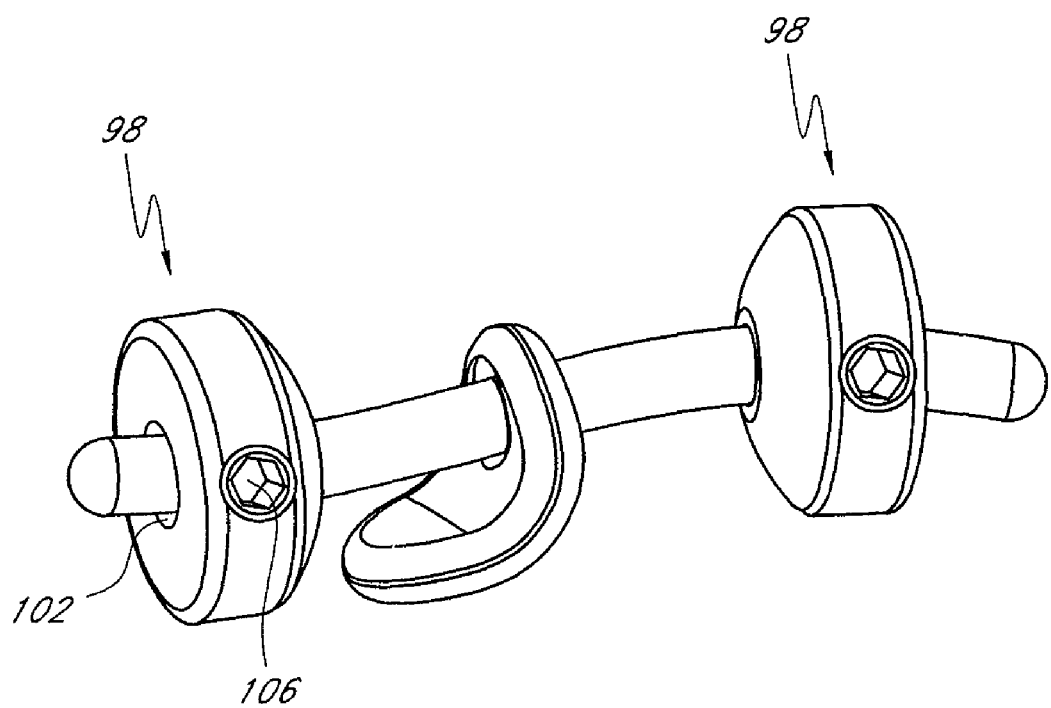
FIG. 29 depicts a preferred embodiment of the invention comprising a curved prosthesis, cable and two set-screw retaining rings.
Figure 30A:
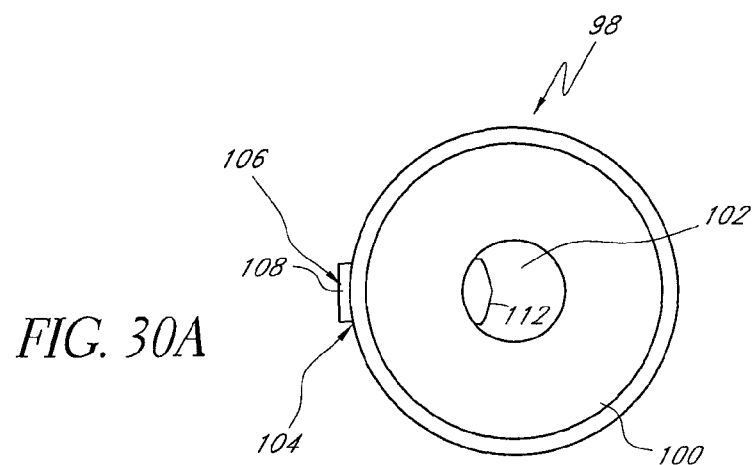
FIGS. 30A and 30B are elevational and cross-sectional views of one embodiment of the set-screw retaining rings, respectively.
Figure 30B:
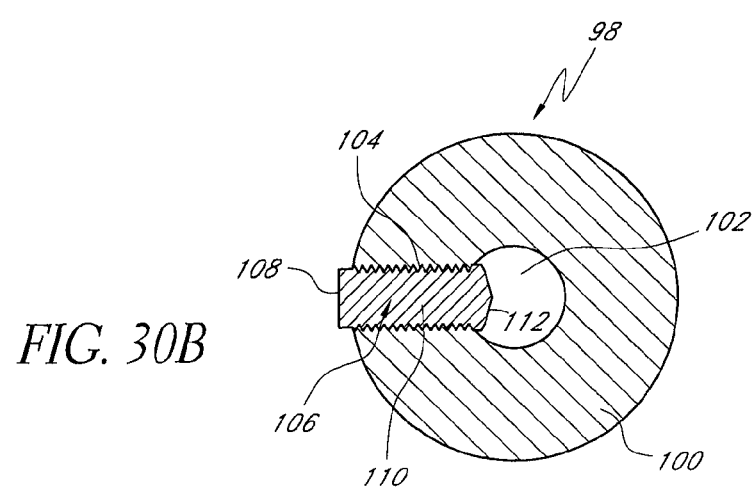
Figure 31:
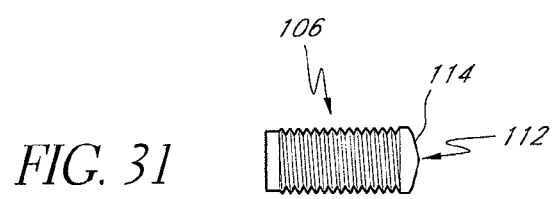
FIGS. 31 through 33 are elevational views of various embodiments of the screw in the set-screw retaining rings.
Figure 32:
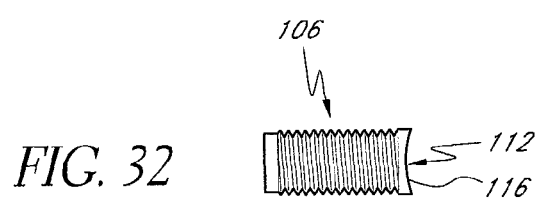
Figure 33:
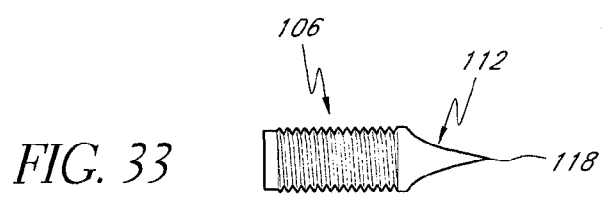

In another embodiment, shown in FIG. 29, the wire or cable is secured to the articular process with retaining rings 98. As depicted in FIGS. 30A and 30B, the retaining rings 98 comprise a ring 100 with a central lumen 102 and a locking element to facilitate locking the ring 100 to a retaining member. The central lumen 102 is adapted to accept insertion of a wire or cable through it. The illustrated locking element is in the form of a side lumen 104 which is threaded and configured to accept a rotatable screw 106 with a proximal end 108, a threaded body 110 and a distal end 112. The threaded body 110 is complementary to the threads of the side lumen 104 so that when the screw 106 is rotated at its distal end 112, the proximal end 108 of the screw 106 moves further into the central lumen 102 and is capable of applying increasing force to a wire or cable inserted through the central lumen 102. In one embodiment, the force on the wire or cable is capable of creating a friction fit or a mechanical interfit to resist movement between the wire or cable and the retaining ring 98, thereby securing the wire or cable to the articular process 20 or 22. As shown in FIGS. 31 to 33, the distal end 112 of the screw 106 can be configured to engage the wire or cable in any of a variety designs, including but no limited to a blunt tip 114, curved tip 116 and piercing tip 118.

In another embodiment, depicted in FIGS. 34A and 34B, the wire or cable is securable to the articular process with a retaining ring 120 have radially inward biased projections 122 defining a central lumen 124. The central lumen has a cross-sectional shape smaller than that of the wire or cable but is capable of enlargement when the inward projections 122 are bent away, as shown in FIGS. 35A and 35B. The inward projections 122 apply increasing force to the wire or cable within the central lumen 124 as the projections 122 are bent, thereby creating a friction fit.

In one embodiment of the invention, one end of the wire or cable retaining member is preformed with a retainer for engaging the articular process. The retainer may be a preformed ring, bulb, flared end, T-bar end, or any of a variety of shapes having a greater cross sectional area than the other portions of the wire or cable retaining member. This configuration of the wire or cable retaining member is adapted to engage an articular process by passing the free end of a wire or cable retaining member through an articular process such that the end with the preformed retainer can engage the articular process.

Figure 36A:
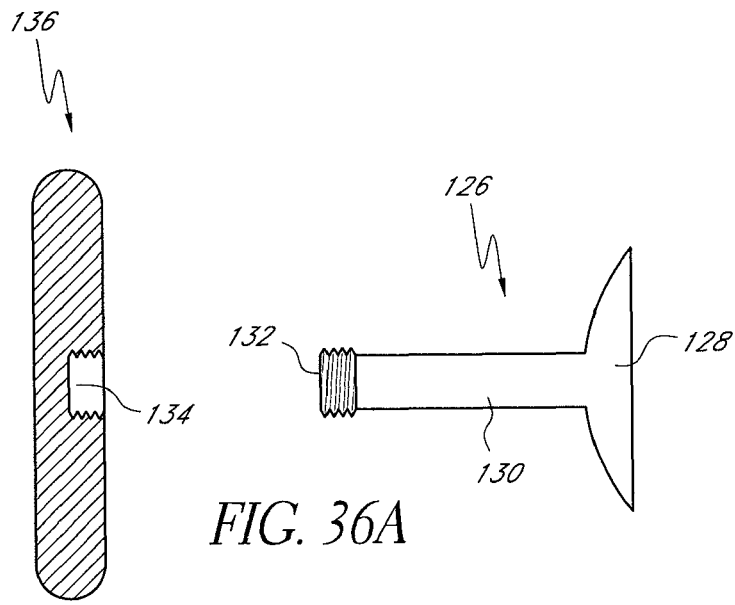
FIGS. 36A to 36C illustrate embodiments of the invention comprising a prosthesis with a close-ended threaded retaining interface and a threaded retaining member.
Figure 36B:
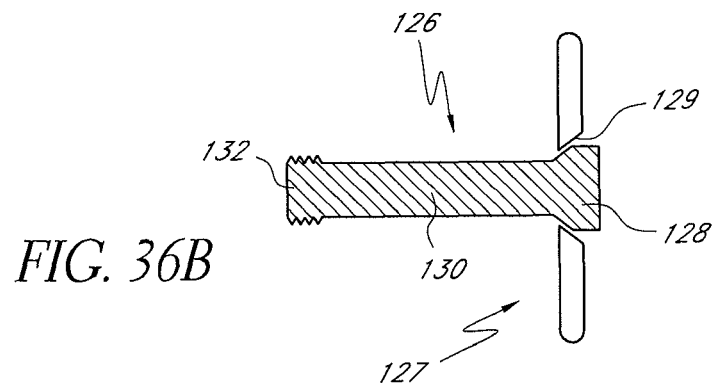
Figure 36C:
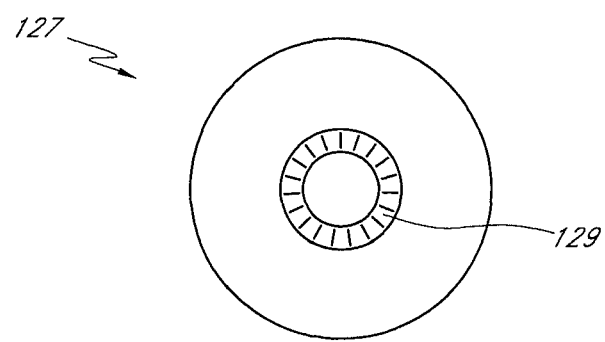

In one embodiment, the wire or cable retaining member is secured to the articular processes with sufficient laxity or length between the secured ends or between the prosthesis and one secured end so that the two articular processes are not fixed in position relative to each other and remain capable of performing movements such as flexion, extension, lateral flexion and/or rotation. In one embodiment, the retaining member comprises a cable of braided polymer, including but not limited to a braided polymer such as PEEK or PEKK, or a braided metal, such as braided cobalt chromium or titanium. The cable can be selected with different degrees of flexibility to provide different degrees of movement at that facet joint. The cable has a first segment capable of engaging the prosthesis at its retaining interface to limit the movement 2. Screw/Bolt Retaining Member In one embodiment of the invention, shown in FIG. 36A, the retaining member comprises a screw or bolt 126 with a proximal end 128, body 130 and distal end 132. The distal end 132 of the screw or bolt is capable of forming a mechanical interfit with a complementary retaining interface 134 on the prosthesis or spacer 136. The distal end 132 typically comprises threads, but one skilled in the art will understand that other configurations may be used to form a mechanical interfit. The complementary retaining interface 134 on the prosthesis 136 could be a threaded through hole or preferably, a close-ended hole. The proximal end 128 of the screw or bolt 126 has a hex or other type of interface known in the art, capable of engaging a rotating tool to manipulate the screw or bolt 126. The body of the screw or bolt 126 has a length sufficient to at least span the length of the hole or conduit created through the articular process for securing the prosthesis. In FIG. 36B, the retaining member further comprises a pivotable washer 127 with a pivot surface 129 that articulates with the proximal end 128 of the screw 126. In one embodiment, the pivotable washer 127 is capable of a range of positions relative to the screw 126 and provides the screw 126 with a better surface area contact with the bone.

Figure 37A:
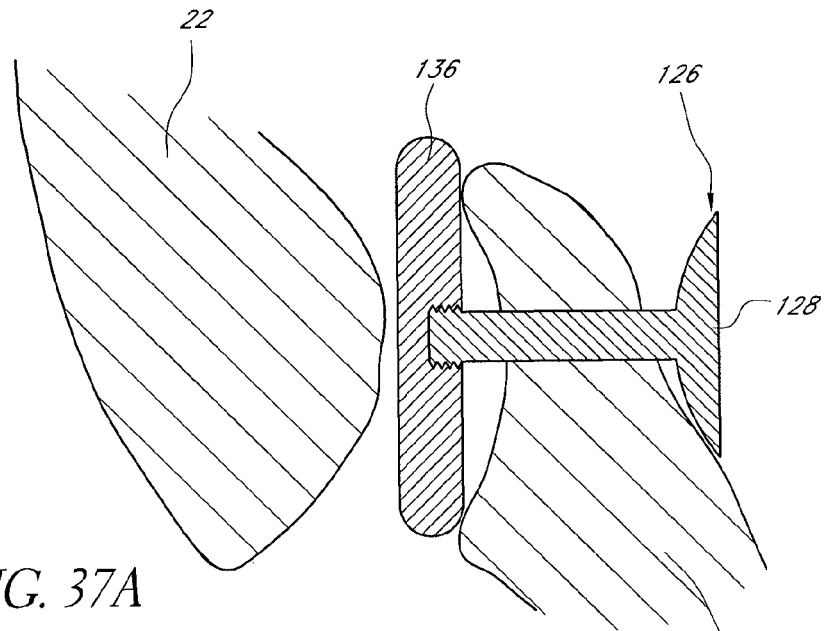
FIG. 37A is a cross sectional view of the prosthesis in FIG. 36A implanted in a facet joint.
Figure 37B:
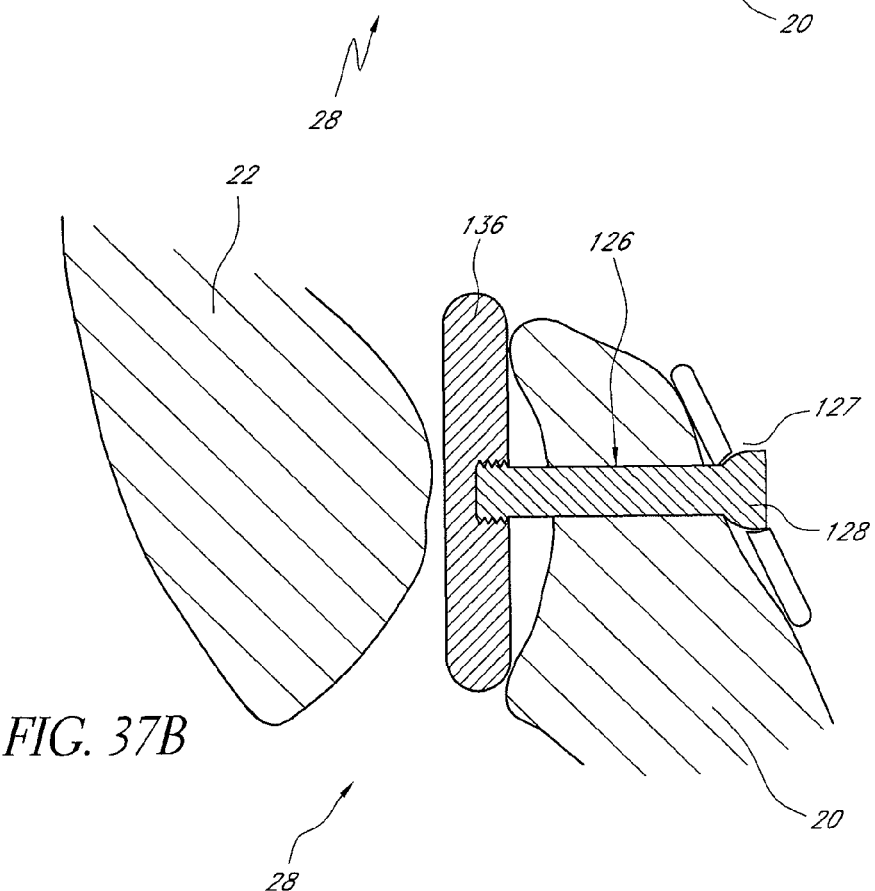
FIG. 37B is a cross sectional view of the prosthesis in FIG. 36B implanted in a facet joint.
Figure 38:
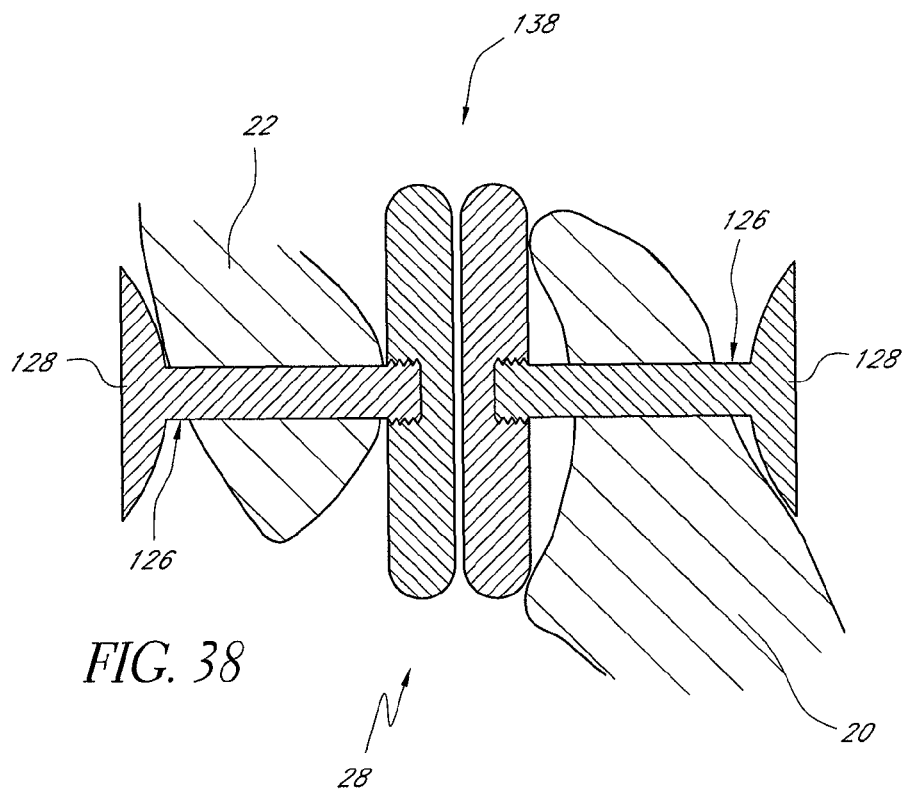
FIG. 38 is a cross sectional view of a two-part prosthesis comprising flat discs implanted into a facet joint.
Figure 39:
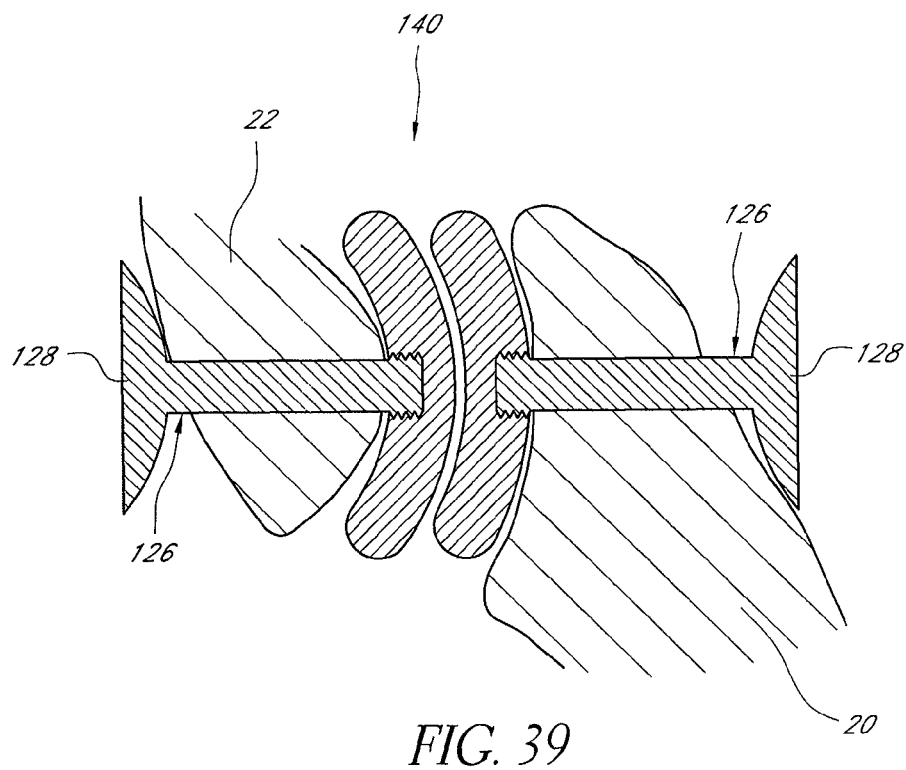
FIG. 39 is a cross sectional view of a two-part prosthesis comprising curved discs implanted into a facet joint.

FIG. 37 is a cross-sectional view of a facet joint 28 with a spacer 136 bolted to one articular process 20 of a facet joint 28. The spacer 136 position is fixed relative to one facet 24 of the joint 28, but provides for spacing and movement of the other facet 26 with respect to the spacer 136. In embodiments of the invention comprising a two-part prosthesis, shown in FIGS. 38 and 39, each disc may have its own screw or bolt retaining member. FIG. 38 depicts a flat two-part prosthesis 138 and FIG. 39 depicts a curved two-part prosthesis 140.

3. Projection Retaining Member

Figure 42:
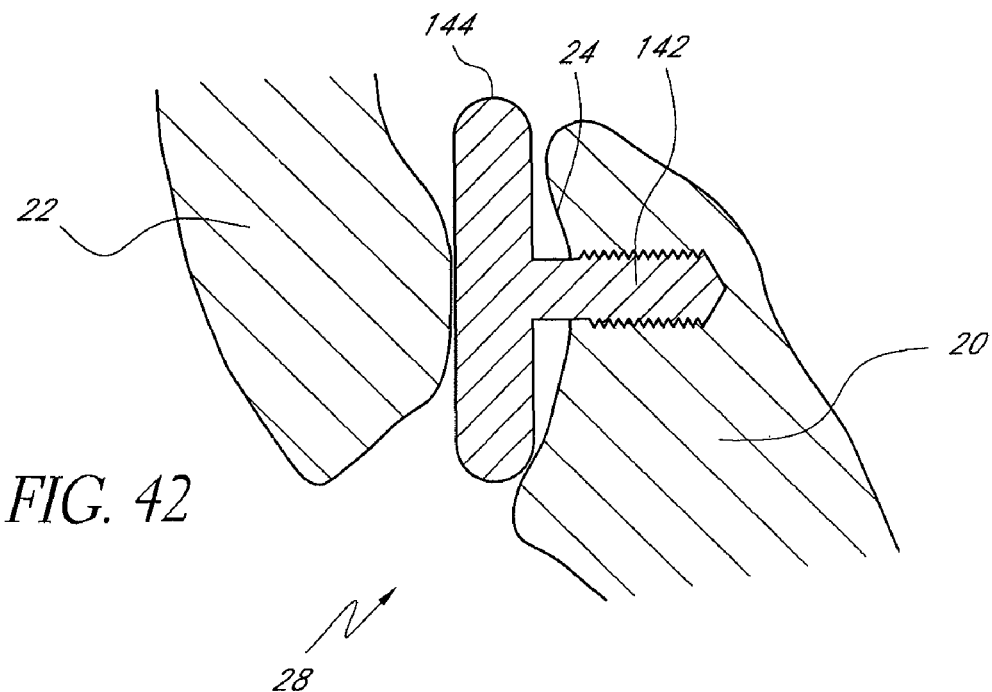
FIG. 42 depicts the prosthesis of FIG. 38A implanted into a facet joint.
Figure 43:
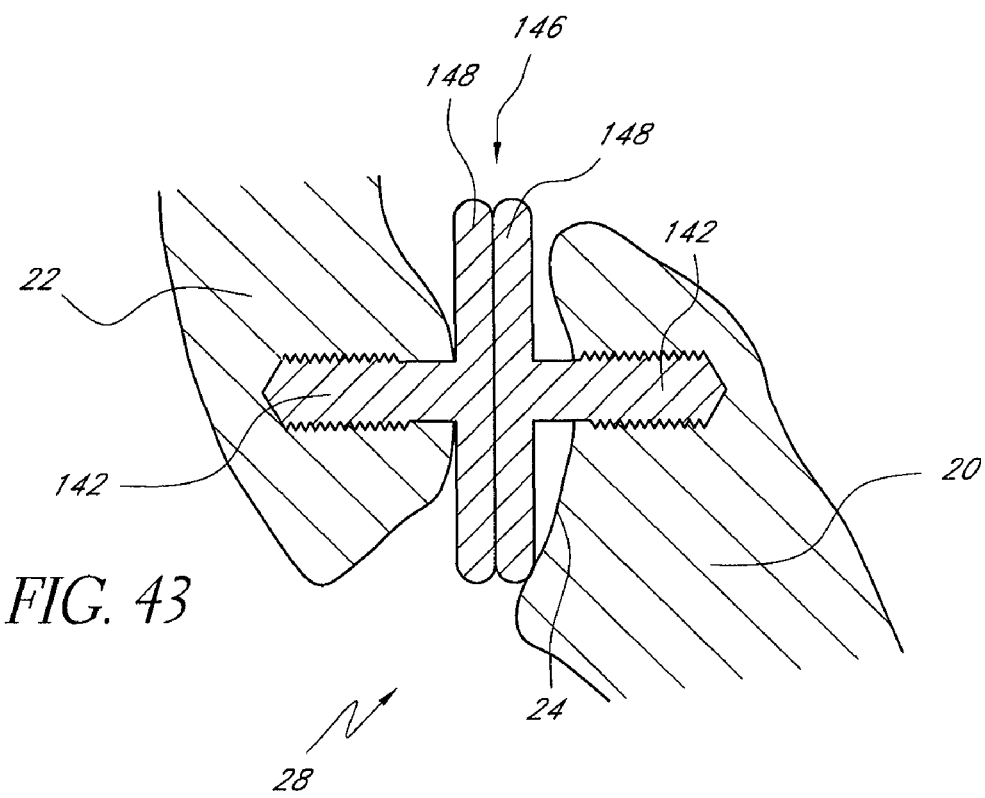
FIG. 43 illustrates a two-part prosthesis implanted into a facet joint.
Figure 44:
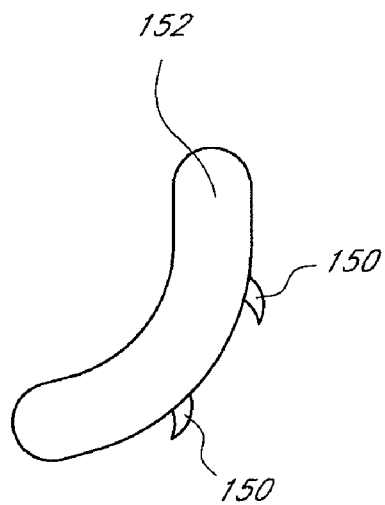
FIG. 44 shows one embodiment of the invention comprising a prosthesis with multiple anchoring projections.
Figure 45:
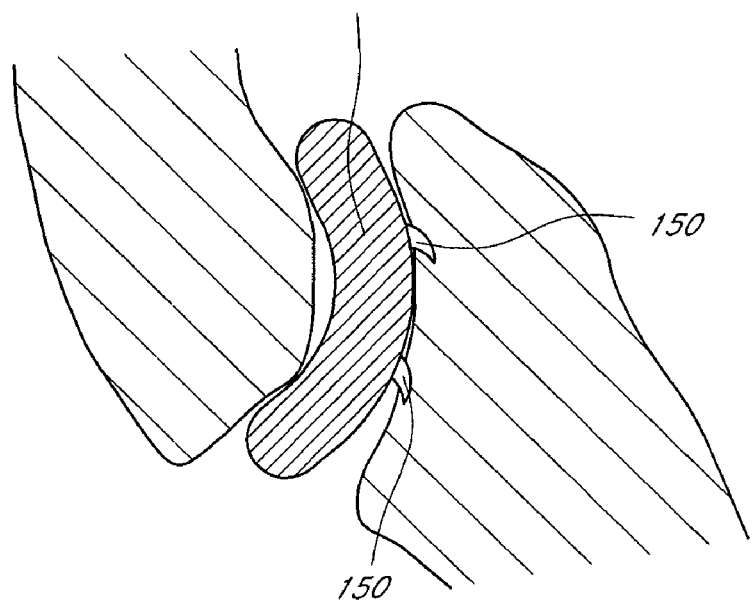
FIG. 45 shows the prosthesis of FIG. 44 implanted into a facet joint.
Figure 46A:
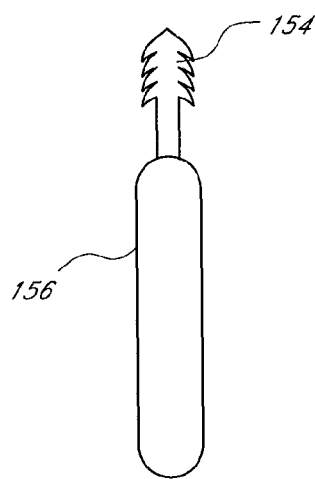
FIGS. 46A and 46B depict one embodiment of the invention comprising a prosthesis with a rigid soft tissue side anchor.
Figure 46B:
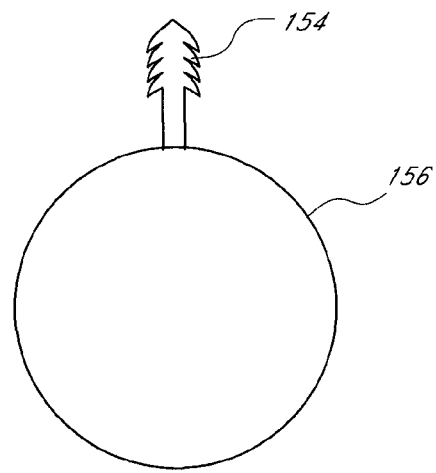

In some embodiments of the invention, shown in FIGS. 40A through 41B, the retaining member is integral with or attached to the prosthesis and comprises a projection 142 from the prosthesis 144 that is adapted to engage the adjacent articular process or surrounding tissue. In one embodiment, the projection comprises at least one spike 142 or hook projecting from one face of the prosthesis 144. In one embodiment, the spike 142 or hook can be ribbed, barbed or threaded to resist separation after insertion into bone or tissue. FIG. 42 depicts the prosthesis 144 of FIG. 40A engaged to a facet 24 of the facet joint 28. In one embodiment comprising a two-part prosthesis 146, shown in FIG. 43, each disc 148 may have its own projection-retaining member 142. In some embodiments of the invention, as depicted in FIG. 44, more than one projection 150 is provided on the prosthesis 152. FIG. 45 illustrates the prosthesis of FIG. 44 placed in a facet joint 28. The projections 150 may be angled with respect to the prosthesis 152 to resist dislodgement by the movement at the joint.

Figure 47A:
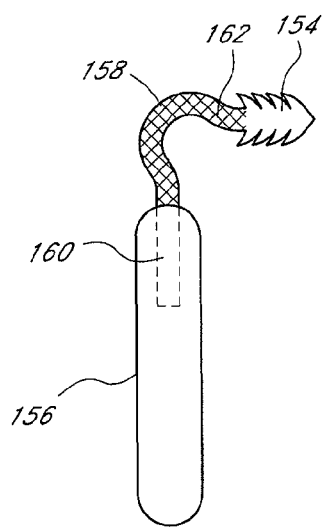
FIGS. 47A and 47B depict one embodiment of the invention comprising a prosthesis with an embedded flexible soft tissue side anchor.
Figure 47B:
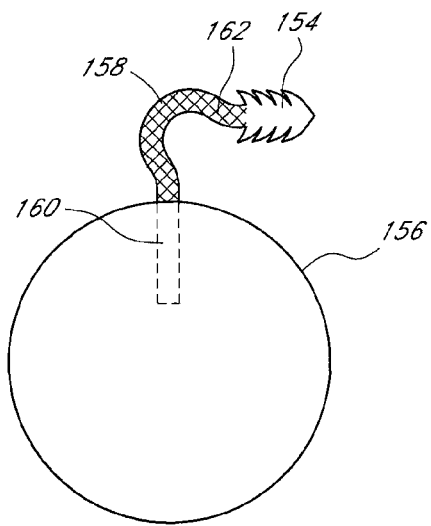

FIGS. 46A to 47B illustrate embodiments of the invention where the retaining member comprises a projection 154 extending laterally such as from the side of the prosthesis 156, and adapted to engage the soft tissue surrounding the facet joint, rather than a bony or cartilaginous articular process. In one example, the prosthesis of FIG. 46 could be inserted into a facet joint through an incision made in the joint capsule, but the integrity of the joint capsule opposite the incision site is maintained and used as an anchoring site for the prosthesis. The orientation of the projection can be fixed as in FIG. 44, or flexible. FIG. 47 depicts a flexible tether such as a wire 158 with its proximal end 160 embedded in or otherwise attached to the prosthesis and one or more barbs which may be attached to its distal end 162. A flexible projection may provide greater selection of soft tissue anchoring sites for the prosthesis.

In one embodiment of the invention, the joint capsule is closed after placement of the prosthesis. Closure may be performed using adhesives, suturing, stapling or any of a variety of closure mechanisms known in the art.

E. Accessing the Facet Joints

1. Surgical Approach to the Cervical Spine

Figure 48:
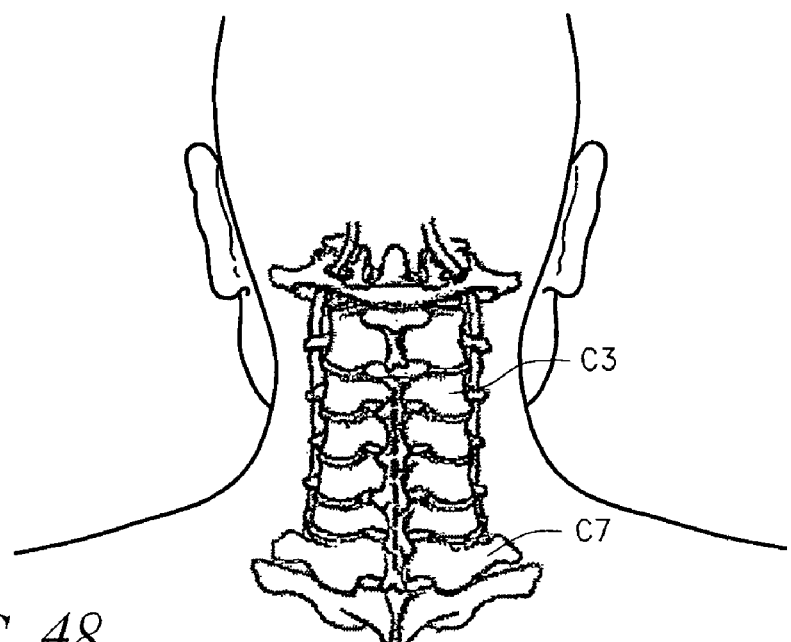
FIG. 48 depicts one embodiment of the invention depicting a posterior surgical approach for implanting a prosthesis in the cervical vertebrae.
Figure 49:
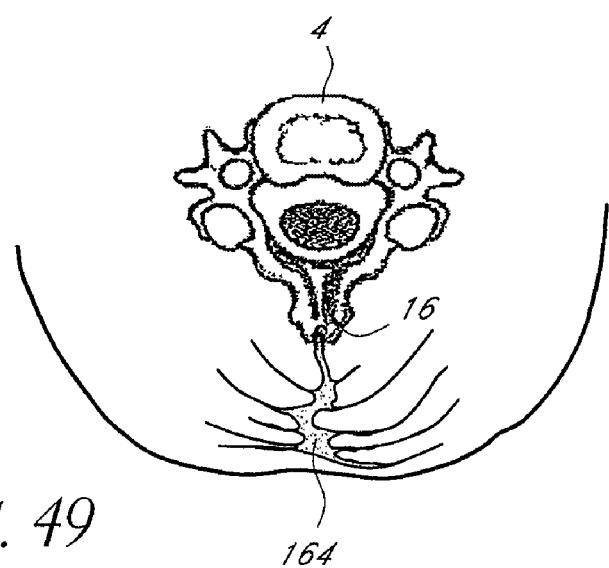
FIG. 49 depicts one embodiment of the invention depicting the cross-sectional surgical approach for implanting a prosthesis in the cervical vertebrae.

In one embodiment of the invention, general anesthesia is achieved and the patient is positioned prone on a turning frame or three-point head rest attached to the table. Skeletal traction is performed using tongs. The patient is prepped and draped in the usual sterile fashion. Pre-operative radiographic films are reviewed and any vertebral anomalies or variations are noted. In one embodiment, the spinous processes are palpated to identify the location of the cervical vertebrae and a skin incision is made over the desired vertebrae, as shown in FIG. 48. In another embodiment, a paraspinous skin incision is made over the desired facet joint. The exposed skin edges and subcutaneous tissue are injected with epinephrine 1:500,000 solution to facilitate hemostasis. Dissection to the spinous processor facet joint is performed using an electrocautery knife. In one embodiment, shown in FIG. 49, dissection is performed along the nuchal ligament 164 to avoid cutting into vascular muscle tissue. Soft tissue retractors are used to maintain tissue tension and aid the dissection process. The ligamentous attachments to the spinous process 16 are detached and the facet joints are exposed. In another embodiment, dissection is performed through the muscle tissue to directly access the facet joint. The joint capsule of the facet joint is opened by incision or piercing. The facets of the facet joint are distracted as required to provide access to the joint space. In one embodiment, the affected facet joint is sized and a joint prosthesis is selected. In one embodiment, the articular process or processes are prepared for receiving the joint prosthesis, including but not limited to roughening the articular surface of the articular process and/or drilling a hole for the prosthesis anchor or retaining member. The prosthesis is inserted into the facet joint space and the anchor or retaining member, if any is attached to the articular process. The steps are repeated until all the joint prostheses have been inserted. The surgical site is closed in layers with a suction tube or drainage tube in place. The surgical site is cleaned and dressed.

2. Surgical Approach to the Thoracic Spine

Figure 50:
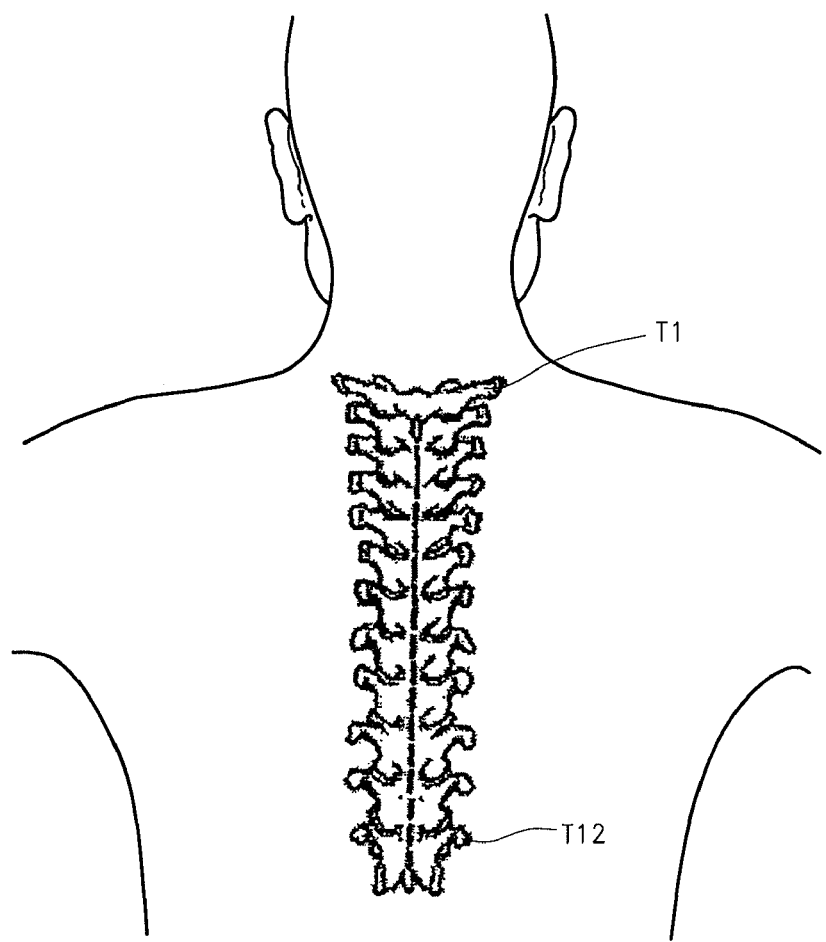
FIG. 50 depicts one embodiment of the invention depicting a posterior surgical approach for implanting a prosthesis in the thoracic vertebrae.

In one embodiment of the invention, general anesthesia is achieved and the patient is positioned prone on a padded spinal operating frame. The patient is prepped and draped in the usual sterile fashion. Pre-operative radiographic films are reviewed and any vertebral anomalies or variations are noted. In one embodiment, shown in FIG. 50, a midline skin incision is made over the desired vertebrae. In another embodiment, a paraspinous skin incision is made over the desired facet joint. The exposed skin edges, subcutaneous tissue and erector spinae muscles are injected with epinephrine 1:500,000 solution to facilitate hemostasis. Dissection is performed using an electrocautery knife or scalpel through the superficial and lumbodorsal fascia to the tips of the spinous processes. The erector spinae muscle is reflected laterally to the tips of the transverse processes, thereby exposing the posterior arch. After exposure of all the desired vertebrae is achieved, an intra-operative x-ray is obtained to confirm access to the desired vertebrae. The facets of the facet joint are distracted as required to provide access to the joint space. The joint capsule of the facet joint is opened by incision or piercing. In one embodiment, the affected facet joint is sized and a joint prosthesis is selected. In one embodiment, the articular process or processes are prepared for receiving the joint prosthesis, including but not limited to roughening the articular surface of the articular process and/or drilling a hole for the prosthesis anchor or retaining member. The prosthesis is inserted into the facet joint space and the anchor or retaining member, if any is attached to the articular process. The steps are repeated until all the joint prostheses have been inserted. The surgical site is closed in layers with a suction tube or drainage tube in place. The surgical site is cleaned and dressed.

3. Surgical Approach to the Lumbar Spine

Figure 51A:
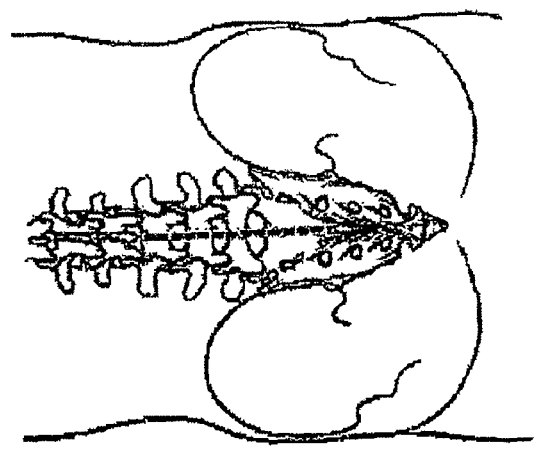
FIGS. 51A to 51E depicts one embodiment of the invention depicting a posterior surgical approach for implanting a prosthesis in the lumbar vertebrae.
Figure 51B:
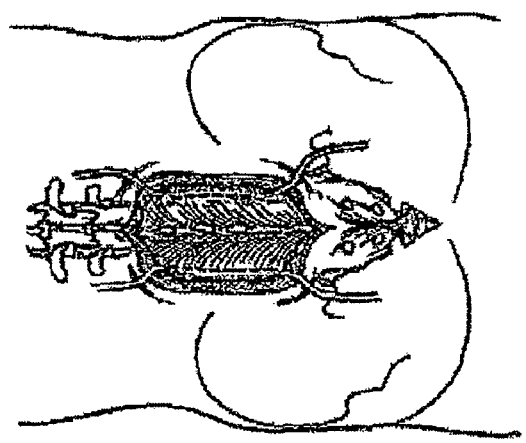
Figure 51C:
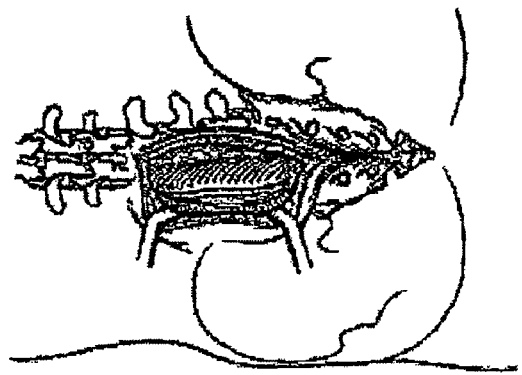
Figure 51D:
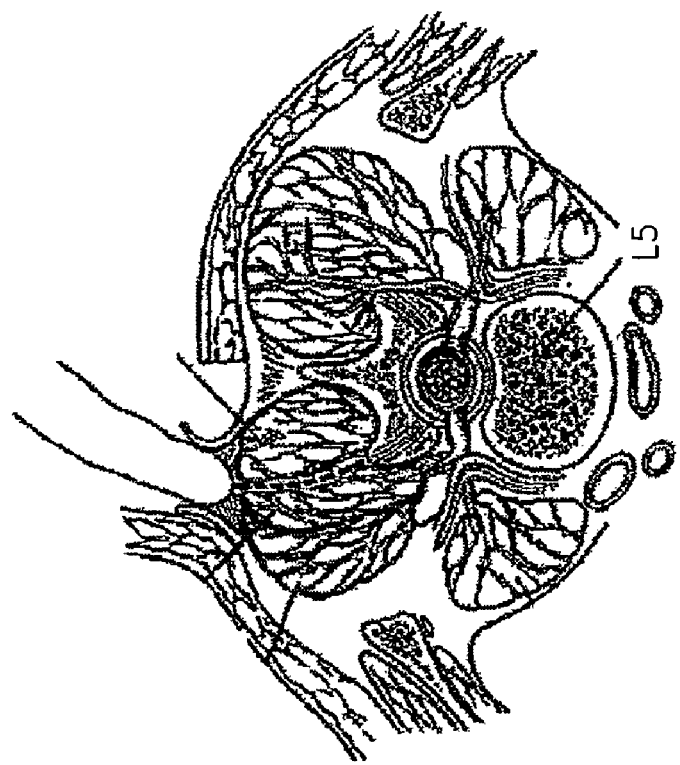
Figure 51E:
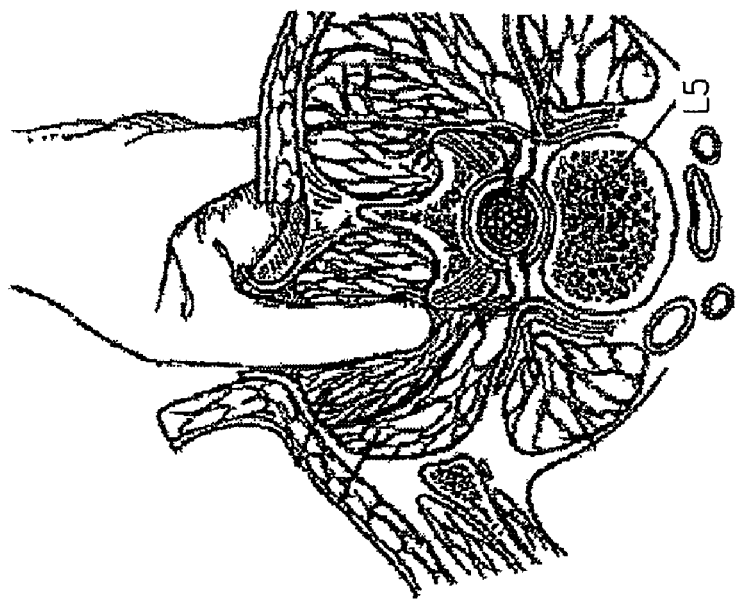

In one embodiment of the invention, general anesthesia is achieved and the patient is positioned prone or kneeling on a padded spinal operating frame. In one embodiment, by allowing the abdomen to hang free, intravenous pressure is reduced and blood loss during the procedure is decreased. The patient is prepped and draped in the usual sterile fashion. Pre-operative radiographic films are reviewed and any vertebral anomalies or variations are noted. FIG. 51A illustrates a midline skin incision is made over the desired vertebrae. The exposed skin edges and subcutaneous tissue are injected with epinephrine 1:500,000 solution to facilitate hemostasis. In FIGS. 51B and 51C, dissection is continued to the lumbodorsal fascia and the surgical site is exposed by retracting the skin and subcutaneous tissue laterally. In FIGS. 51D and 51E, blunt finger dissection is used between the multifidus and longissimus muscles to access the facet joints. Self-retaining Gelpi retractors are inserted between the muscle groups. Electrocautery or elevators are used to separate the transverse fibers of the multifidus from their heavy fascial attachments. Exposure of the transverse processes and fascial planes is continued. Cautery may be used to provide hemostasis from the lumbar arteries and veins along the base of the transverse processes. The facets of the facet joint are distracted as required to provide access to the joint space. The joint capsule of the facet joint is opened by incision or piercing. In one embodiment, the affected facet joint is sized and a joint prosthesis is selected. In one embodiment, the articular process or processes are prepared for receiving the joint prosthesis, including but not limited to roughening the articular surface of the articular process and/or drilling a hole for the prosthesis anchor or retaining member. The prosthesis is inserted into the facet joint and the anchor or retaining member, if any is attached to the articular process. The steps are repeated until all the joint prostheses have been inserted. The surgical site is closed in layers over a suction tube and the skin flaps are sutured down to the fascia to eliminate any dead space in the tissue. The surgical site is cleaned and dressed.

4. Minimally Invasive Approach to the Cervical Spine

In one embodiment of the invention, general or local anesthesia is achieved and the patient is positioned prone on a turning frame or three-point head rest attached to the table. Skeletal traction is performed using tongs. The patient is prepped and draped in the usual sterile fashion. Pre-operative radiographic films are reviewed and any vertebral anomalies or variations are noted. The spinous processes are palpated to identify the location of the cervical vertebrae and a small 1 cm skin incision is made over the desired insertion site. Hemostasis is achieved with infiltration of epinephrine 1:500,000 solution around the incision site. Under fluoroscopy, a trocar or needle is inserted through the incision site and joint capsule to the desired facet joint. The needle or trocar is replaced with an introducer. In one embodiment, insertion is performed along the nuchal ligament to avoid cutting into vascular muscle tissue. In another embodiment, insertion is performed directly through the skin and muscle overlying the facet joint. The facets of the facet joint are distracted as required to provide access to the joint space. In one embodiment, the affected facet joint is sized by injecting a radio-contrast agent into the facet joint and a joint prosthesis is selected. In one embodiment, the articular process or processes are prepared for receiving the joint prosthesis, including but not limited to roughening the articular surface of the articular process and/or drilling a hole using endoscopic instruments known in the art. The prosthesis is inserted into the facet joint space through the introducer and an anchor or retaining member, if any is attached to the articular process. The steps are repeated until all the joint prostheses have been inserted. The surgical site is closed, cleaned and dressed.

5. Minimally Invasive Approach to the Thoracic Spine

In one embodiment of the invention, general or local anesthesia is achieved and the patient is positioned prone on a padded spinal operating frame. The patient is prepped and draped in the usual sterile fashion. Pre-operative radiographic films are reviewed and any vertebral anomalies or variations are noted. A small 1 cm skin incision is made over the desired insertion site. Hemostasis is achieved by injecting epinephrine 1:500,000 solution around the incision site. Under fluoroscopy, a trocar or needle is inserted through the superficial and lumbodorsal fascia, the erector spinae muscle and joint capsule to access the facet joint. The trocar or needle is replaced with an introducer. The facets of the facet joint are distracted as required to provide access to the joint space. An intra-operative x-ray or fluoroscopy is obtained to confirm access to the desired facet joint. In one embodiment, the affected facet joint is sized and a joint prosthesis is selected. In one embodiment, the articular process or processes are prepared for receiving the joint prosthesis, including but not limited to roughening the articular surface of the articular process and/or drilling a hole for the prosthesis anchor or retaining member, using endoscopic instruments known in the art. The prosthesis is inserted into the facet joint space and the anchor or retaining member, if any is attached to the articular process. The steps are repeated until all the joint prostheses have been inserted. The surgical site is closed, cleaned and dressed.

6. Minimally Invasive Approach to the Lumbar Spine

In one embodiment of the invention, general or local anesthesia is achieved and the patient is positioned prone or kneeling on a padded spinal operating frame. In one embodiment, by allowing the abdomen to hang free, intravenous pressure is reduced and blood loss during the procedure is decreased. The patient is prepped and draped in the usual sterile fashion. Pre-operative radiographic films are reviewed and any vertebral anomalies or variations are noted. A small 1 cm skin incision is made over the desired insertion site. Hemostasis is achieved by injecting epinephrine 1:500,000 solution around the incision site. Under fluoroscopy, a trocar or needle is inserted through the lumbodorsal fascia. The trocar or needle is replaced with an introducer. In one embodiment, radio-contrast agent is injected through the introducer to identify the junction between the lumbodorsal fascia and the multifidus and longissimus muscles. A blunt dissector is inserted through the introducer to dissect between the multifidus and longissimus muscles and pierce the joint capsule to access the facet joints. The facets of the facet joint are distracted as required to provide access to the joint space. In one embodiment, the affected facet joint is sized and a joint prosthesis is selected. In one embodiment, the articular process or processes are prepared for receiving the joint prosthesis, including but not limited to roughening the articular surface of the articular process and/or drilling a hole for the prosthesis anchor or retaining member. The prosthesis is inserted into the facet joint space and the anchor or retaining member, if any is attached to the articular process. The steps are repeated until all the joint prostheses have been inserted. The surgical site is closed, cleaned and dressed.

While embodiments of this invention have been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method of treating vertebral dysfunction, comprising:
   opening a facet joint capsule between a first facet and a second facet of adjacent vertebral bodies;
   forming a hole through the first facet and second facet;
   distracting the adjacent vertebral bodies from a first spacing to a second spacing;
   placing a spacer between the first facet and second facet to maintain the second spacing;
   threading a retainer through the hole of the first facet;
   threading the retainer through a hole in the spacer;
   threading the retainer through the hole of the second facet; and
   enlarging at least one end of the retainer.

2. The method of claim 1, wherein the step of enlarging at least one end of the retainer comprises:
   tying a knot in at least one end of the retainer.

3. The method of claim 1, wherein the step of enlarging at least one end of the retainer comprises:
   threadably engaging an anchor to at least one end of the retainer.

4. The method of claim 1, further comprising the step of:
conforming the shape of at least a portion of the spacer to at least a portion of a facet of the facet joint.

5. The method of claim 4, wherein the conforming step is performed after the placing step.

6. The method of claim 4, wherein the conforming step is performed while the spacer is generally located between the facets of the facet joint.

7. The method of claim 1, wherein the step of enlarging at least one end of the retainer comprises securing an enlarged structure on at least one end of the retainer.

8. The method of claim 1, wherein the step of enlarging at least one end of the retainer comprises securing a retaining ring comprising a set-screw structure on at least one end of the retainer.

9. A method of treating vertebral dysfunction, comprising:
opening a facet joint capsule between a first facet and a second facet of adjacent vertebral bodies;
forming a hole through the first facet and second facet;
distracting the adjacent vertebral bodies from a first spacing to a second spacing;
placing a spacer between the first facet and second facet to maintain the second spacing, the spacer including an hole extending between a first face and a second face of the spacer;
threading a retainer through the hole of the first facet;
threading the retainer through the hole in the spacer; and
threading the retainer through the hole of the second facet to retain the spacer within the facet joint.

10. The method of claim 9, further comprising the step of conforming the shape of at least a portion of the spacer to at least a portion of a facet of the facet joint.

11. The method of claim 10, wherein the conforming step is performed after the placing step.

12. The method of claim 10, wherein the conforming step is performed while the spacer is generally located between the facets of the facet joint.

* * * * *